(12) United States Patent
Fuertinger et al.

(10) Patent No.: US 12,106,831 B2
(45) Date of Patent: Oct. 1, 2024

(54) TECHNIQUES FOR CONDUCTING VIRTUAL CLINICAL TRIALS

(71) Applicant: Fresenius Medical Care Holdings, Inc., Waltham, MA (US)

(72) Inventors: Doris H. Fuertinger, Long Island City, NY (US); Alice Topping, New York, NY (US); Franz Kappel, Graz (AT); Stephan Thijssen, New York, NY (US); Peter Kotanko, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 18 days.

(21) Appl. No.: 17/668,418

(22) Filed: Feb. 10, 2022

(65) Prior Publication Data

US 2022/0270719 A1 Aug. 25, 2022

Related U.S. Application Data

(63) Continuation of application No. 16/032,972, filed on Jul. 11, 2018, now Pat. No. 11,282,590.

(Continued)

(51) Int. Cl.
| | |
|---|---|
| *G16H 10/20* | (2018.01) |
| *G16H 50/50* | (2018.01) |
| *G16H 50/70* | (2018.01) |

(52) U.S. Cl.
CPC .......... *G16H 10/20* (2018.01); *G16H 50/50* (2018.01); *G16H 50/70* (2018.01)

(58) Field of Classification Search
CPC ......... G16H 50/50; G16H 10/20; G16H 50/20
See application file for complete search history.

(56) References Cited

U.S. PATENT DOCUMENTS

| | | | |
|---|---|---|---|
| 2007/0038475 A1 | 2/2007 | Schlessinger | |
| 2013/0041683 A1* | 2/2013 | Boissel | G16B 40/20 |
| | | | 705/2 |

(Continued)

FOREIGN PATENT DOCUMENTS

| | | | | |
|---|---|---|---|---|
| WO | WO-2006084196 A2 * | 8/2006 | ........... | G06F 19/324 |

OTHER PUBLICATIONS

Spanakis, Marios, et al. "Exploitation of patient avatars towards stratified medicine through the development of in silico clinical trials approaches." 13th IEEE International Conference on BioInformatics and BioEngineering. IEEE, 2013. (Year: 2013).*

*Primary Examiner* — Jason B Dunham
*Assistant Examiner* — Constantine Siozopoulos
(74) *Attorney, Agent, or Firm* — KDW Firm PLLC

(57) ABSTRACT

Techniques and apparatus for generating, performing, and evaluating virtual clinical trials that include clinic modules to represent real-world operational aspects of trial entities are described. In one embodiment, for example, an apparatus may include at least one memory, and logic coupled to the at least one memory. The logic may be configured to generate a plurality of avatars configured to model a health condition associated with a population of patients, and to perform a virtual clinical trial to simulate a course of treatment for the plurality of avatars, the virtual clinical trial to include at least one clinic module associated with at least one event and a probability for the at least one event, the at least one event to model an operational aspect of an entity of the virtual clinical trial. Other embodiments are described.

20 Claims, 23 Drawing Sheets

Related U.S. Application Data

(60) Provisional application No. 62/531,810, filed on Jul. 12, 2017.

(56) References Cited

U.S. PATENT DOCUMENTS

| | | |
|---|---|---|
| 2014/0200181 A1 | 7/2014 | Fuertinger |
| 2016/0180053 A1 | 6/2016 | Fuertinger |
| 2016/0253473 A1* | 9/2016 | Anderson .............. G16H 50/70 705/2 |

* cited by examiner

Table 1: Characteristics of patients with Avatars, the reference population and the comparator group.

| | Avatars | Reference population | Comparator group |
|---|---|---|---|
| Number of patients | 6,659 | 79,426 | 6,659 |
| Male (%) | 54% | 55% | 55% |
| Race (white) | 57% | 61% | 62% |
| Age (years) | 64.1±13.9 | 65.6±14 | 65.9 ± 13.8 |
| Body mass index (kg/m2) | 29.4 ± 7.6 | 29.1±7.5 | 29.4 ± 7.4 |
| Vintage (years) | 3.4 (1.7, 5.8) | 2.3 (0.7, 5.5) | 2.4 (0.7, 4.9) |
| Comorbid diabetes (%) | 64% | 64.50% | 64.70% |
| Hemoglobin (mg/dL) | 10.6±0.5 | 10.7±0.7 | 10.7±0.7 |
| Pre-treatment weight (kg) | 81.8 (68.6, 98.1) | 81.4 (68.1, 98) | 81.6 (68.4, 98.1) |
| Pre-treatment SBP (mmHg) | 150.1±17.6 | 148.5±18.4 | 148.3±18.4 |
| Post-treatment SBP (mmHg) | 138.2 ± 16 | 137.9±16.4 | 137.6±16.4 |
| Treatment time | 221.3±25.4 | 222.7±28.6 | 222±29.1 |
| Ultrafiltration volume (kg) | 2.44±0.93 | 2.3±0.9 | 2.34±0.92 |
| Interdialytic weight gain (%) | 3 (2.3, 3.6) | 2.9 (2.3, 3.5) | 2.9 (2.3, 3.5) |
| Albumin (g/dL) | 3.9±0.32 | 3.8±0.4 | 3.8±0.4 |
| Iron dose (mcg/month) | 250 (150, 500) | 250 (150, 500) | 250 (150, 500) |
| Dialysate sodium (mEq/L) | 137 (137, 138) | 137 (137, 138) | 137 (137, 138) |
| Neutrophils to lymphocytes ratio | 3.6 (2.7, 5) | 3.7 (2.7, 5.2) | 3.7 (2.7, 5.2) |
| Transferrin saturation | 34 ± 8.1 | 33.6 ± 8.9 | 33.7 ± 8.7 |

*FIG. 17*

Table 2: Overall ESA doses and hemoglobin results

| | No. | Total doses | Average ESA dose* | ESA dose per-HD treatment** | ESA dose per patient year | Average Hemoglobin |
|---|---|---|---|---|---|---|
| VIAT 1.0 | 6,659 | 97573 | 138,789.4 | 16.1 (8.1, 32.3) | 2037.2 | 11.4 ± 3.4 |
| VIAT 2.0 | 6,659 | 87798 | 95,984.2 | 8.1 (4, 16.1) | 1267.6 | 11 ± 1 |
| VIAT 3.0 | 6,659 | 86471 | 97,154.8 | 8.1 (4, 16.1) | 1263.8 | 10.9 ± 1.1 |
| Clinical data | 6,659 | 85596 | 92,551.4 | 8.3 (6.2, 16.5) | 1335.6 | 10.8 ± 1.1 |

*Mean ± standard deviation
**Median (25th percentile, 75th percentile)

FIG. 18

Table 3: ESA doses per category of average monthly hemoglobin

| Hgb category | Data | % of patients | Number of ESA doses per month* | Monthly cumulative ESA doses* | ESA dose per HD -treatment* |
|---|---|---|---|---|---|
| <8.0 | VIAT 1.0 | 8.4 | 2.2±0.5 | 372.9±161.5 | 30.1±13 |
|  | VIAT 2.0 | 0.4 | 2.5±0.6 | 494.9±99.2 | 39.9±8 |
|  | VIAT 3.0 | 0.6 | 2±0.6 | 339.1±156.6 | 27.3±12.6 |
|  | Clinical data | 1.1 | 1.7±1.1 | 335.9±207.2 | 27.8±17.1 |
| 8.0–10.0 | VIAT 1.0 | 21.5 | 2.1±0.4 | 337.2±149.5 | 27.2±12.1 |
|  | VIAT 2.0 | 10.4 | 2.1±0.6 | 279.1±160.4 | 22.6±12.9 |
|  | VIAT 3.0 | 12.2 | 1.8±0.6 | 241.1±152.5 | 19.4±12.3 |
|  | Clinical data | 18.1 | 1.9±0.9 | 236±167 | 19.5±13.8 |
| 10.0–11.0 | VIAT 1.0 | 24.1 | 1.6±0.9 | 148.3±120.6 | 12.3±10 |
|  | VIAT 2.0 | 46.2 | 1.7±0.7 | 202.5±148.9 | 16.3±12 |
|  | VIAT 3.0 | 43.0 | 1.4±0.7 | 132.5±113.1 | 10.7±9.1 |
|  | Clinical data | 39.3 | 1.4±0.7 | 137.3±115.8 | 11.1±9.3 |
| 11.0–12.0 | VIAT 1.0 | 18.5 | 0.9±0.8 | 133.9±93.5 | 10.8±7.5 |
|  | VIAT 2.0 | 32.5 | 0.7±0.7 | 96.5±70.5 | 7.8±5.7 |
|  | VIAT 3.0 | 32.8 | 0.8±0.7 | 96.8±72.4 | 7.8±5.8 |
|  | Clinical data | 32.6 | 0.9±0.8 | 108.4±83.8 | 9±6.9 |
| 12.0–14.0 | VIAT 1.0 | 14.1 | 0.1±0.4 | 106.7±49.9 | 8.6±4 |
|  | VIAT 2.0 | 9.7 | 0.1±0.3 | 101.6±45.6 | 8.2±3.7 |
|  | VIAT 3.0 | 10.6 | 0.1±0.3 | 99.4±47.6 | 8±3.8 |
|  | Clinical data | 8.6 | 0.3±0.6 | 108.9±77.8 | 9±6.4 |
| >14.0 | VIAT 1.0 | 13.4 | 0±0.1 | 98.3±45.1 | 8±3.6 |
|  | VIAT 2.0 | 0.9 | 0±0.1 | 150±0 | 12.1±0 |
|  | VIAT 3.0 | 0.8 | 0±0.2 | 130.4±28 | 10.5±2.3 |
|  | Clinical data | 0.3 | 0.1±0.4 | 125±75.6 | 10.3±6.2 |

*Mean ± standard deviation

*FIG. 19*

Table 4: Patient characteristics of patients for whom Avatars where built, of the FKC reference group, and three randomly sampled comparator groups.

| | Avatars | Reference_population | Random group 1 | Random group 2 | Random group 3 |
|---|---|---|---|---|---|
| No. of Patients | 6,659 | 79,426 | 6,659 | 6,659 | 6,659 |
| Male (%) | 54% | 55% | 56% | 55% | 55% |
| Race (white) | 57% | 61% | 61% | 62% | 66% |
| Age (years) | 64.1±13.9 | 65.6±14 | 65.8±14 | 65.9±13.8 | 65.9±14.1 |
| Body mass index (kg/m2) | 29.4 ± 7.6 | 29.1±7.5 | 29.1 ± 7.3 | 29.4±7.4 | 29 ± 7.5 |
| Vintage (years) | 3.4 (1.7, 5.8) | 2.3 (0.7, 5) | 2.3 (0.6, 4.92) | 2.3 (0.7, 4.9) | 2.3 (0.7, 4.9) |
| Comorbid diabetes (%) | 64% | 64.55% | 64% | 64.70% | 65% |
| Hemoglobin (mg/dL) | 10.6±0.5 | 10.7±0.7 | 10.7±0.71 | 10.7±0.7 | 10.7±0.7 |
| Pre-treatment weight (kg) | 81.8 (68.6, 98.1) | 81.4 (68.1, 98) | 81.1 (68.9, 98.4) | 81.6 (68.4, 98.1) | 81.3 (68, 98) |
| Pre-treatment SBP (mmHg)* | 150.1±17.6 | 148.5±18.4 | 148.1±18.6 | 148.3±18.4 | 148.5±18.5 |
| Post-treatment SBP (mmHg) | 138.2±16 | 137.9±16.4 | 137.7±16.5 | 137.6±16.4 | 138.1±16.6 |
| Treatment time | 221.3±25.4 | 222.7±28.6 | 222.8±28 | 222±28.1 | 222.3±27.3 |
| Ultrafiltration volume (kg) | 2.44±0.93 | 2.3±0.9 | 2.34±0.92 | 2.34±0.92 | 2.33±0.9 |
| Interdialytic weight gain (%) | 3 (2.3, 3.6) | 2.9 (2.3, 3.5) | 2.8 (2.2, 3.5) | 2.9 (2.3, 3.5) | 2.8 (2.2, 3.5) |
| Albumin (g/dL) | 3.9±0.32 | 3.8±0.4 | 3.8±0.4 | 3.8±0.4 | 3.8±0.4 |
| Iron dose (mcg/month) | 250 (150, 500) | 250 (150, 500) | 250 (150, 500) | 250 (150, 500) | 250 (150, 500) |
| Dialysate sodium (mEq/L) | 137 (137, 138) | 137 (137, 138) | 137 (137, 138) | 137 (137, 138) | 137 (137, 138) |
| Neutrophils to lymphocytes ratio | 3.6 (2.7, 5) | 3.7 (2.7, 5.2) | 3.7 (2.7, 5.2) | 3.7 (2.7, 5.2) | 3.7 (2.7, 5.2) |
| Transferrin saturation (%) | 34±8.1 | 33.6±8.9 | 33.5±8.9 | 33.7±8.7 | 33.7±9 |

*systolic blood pressure

FIG. 20

TECHNIQUES FOR CONDUCTING VIRTUAL CLINICAL TRIALS

CROSS-REFERENCE TO RELATED APPLICATION

This application is a Continuation Application of U.S. application Ser. No. 16/032,972, filed Jul. 11, 2018, which claims priority to U.S. Provisional Patent Application Ser. No. 62/531,810, filed on Jul. 12, 2017, entitled "Virtual Clinical Trial Controller," the contents of which are incorporated herein by reference.

TECHNICAL FIELD

Embodiments herein generally relate to processes and apparatuses operative to perform and evaluate virtual clinical trials and, in particular, in silico clinical trials of virtual dialysis patients.

BACKGROUND

Clinical trials are performed to evaluate healthcare systems targeted for use with patients, such as treatment methods, pharmaceuticals, and medical devices. Randomized controlled trials (RCTs) are a standard trial conducted when seeking approval of healthcare systems, for example, by the U.S. Food and Drug Administration (FDA). By randomly allocating subjects to two or more treatment groups, RCTs randomize confounding factors in an effort to eliminate bias. Consequently, a well-designed and properly conducted RCT may provide unbiased results and have minimal risk of systematic errors, therefore having a high internal validity.

However, conventional RCTs using actual patients may be limited. For example, RCTs may lack generalizability because RCT participants may be not representative of the wider population of interest, and, therefore, such RCTs may have poor external validity. In another example, conventional RCTs typically lack sufficient ecological validity because they do not sufficiently generalize to the real-life and clinical settings in which the trial results may later be applied. In addition, RCTs may suffer from the need to recruit a sufficiently large number of patients to conduct a properly powered study, associated high costs, the need to establish a sophisticated trial infrastructure, and the long duration from study inception to completion. With multiple treatments in the pipeline, companies and academic institutions compete for a limited pool of patients. For example, in the field of oncology it has been estimated that only 20% of patients are eligible for clinical trials, since many patients are excluded because of poor performance status or inability to meet specific eligibility requirements. In addition, for studies involving smaller population groups, such as pancreatic cancer, a high percentage of patient participation would be required (for instance, 80%) to have a sufficient trial population, yet a small percentage (for instance, 5%) may actually volunteer to participate.

Accordingly, although they provide useful information, conventional clinical trials, such as RCTs, may be unable to adequately evaluate healthcare systems. It is with these considerations in mind that the present disclosure may be useful.

SUMMARY

In accordance with various aspects of the described embodiments is an apparatus, comprising at least one memory, and logic coupled to the at least one memory, the logic to generate a plurality of avatars configured to model a health condition associated with a population of patients, and perform a virtual clinical trial to simulate a course of treatment for the plurality of avatars, the virtual clinical trial to include at least one clinic module associated with at least one event and a probability for the at least one event, the at least one event to model an operational aspect of an entity of the virtual clinical trial.

In some embodiments, the health condition may include anemia. In various embodiments, the population of patients may include dialysis patients. In exemplary embodiments, the virtual clinical trial may include a virtual anemia trial to simulate a treatment protocol for anemia. In various embodiments, the apparatus may include logic to determine results of the virtual anemia trial, the results may include hemoglobin levels or erythropoiesis stimulating agents (ESA) dosage, or a combination thereof. In some embodiments, the apparatus may include logic to generate a recommended course of treatment based on the results. In some embodiments, the at least one clinic module may include a laboratory module, a physician module, a dialysis facility module, or a hospital module, or any combination thereof. In some embodiments, the at least one event may include measurement noise, patient non-adherence, or patient non-attendance, or any combination thereof. In various embodiments, the at least one clinic module may include a laboratory module, and the at least one event may comprise a sample shipping schedule, a sample processing time, a sample processing error, or an unusable sample, or any combination thereof. In some embodiments, the apparatus may include logic to determine the probability of the at least event based on real-world clinical data.

In accordance with various aspects of the described embodiments is a method that may include the steps of generating a plurality of avatars configured to model a health condition associated with a population of patients, and performing a virtual clinical trial to simulate a course of treatment for the plurality of avatars, the virtual clinical trial to include at least one clinic module associated with at least one event and a probability for the at least one event, the at least one event to model an operational aspect of an entity of the virtual clinical trial.

In some embodiments, the health condition of the method may include anemia. In some embodiments, the population of patients of the method may include dialysis patients. In some embodiments, the virtual clinical trial of the method may include a virtual anemia trial to simulate a treatment protocol for anemia. In some embodiments, the method may include determining results of the virtual anemia trial, the results comprising hemoglobin levels or erythropoiesis stimulating agents (ESA) dosage, or a combination thereof. In some embodiments, the method may include generating a recommended course of treatment based on the results. In some embodiments, the at least one clinic module of the method may include a laboratory module, a physician module, a dialysis facility module, or a hospital module, or any combination thereof. In some embodiments, the at least one event of the method may include measurement noise, patient non-adherence, or patient non-attendance, or any combination thereof. In some embodiments, the at least one clinic module of the method may include a laboratory module, and the at least one event may comprise a sample shipping schedule, a sample processing time, a sample processing error, or an unusable sample, or any combination thereof. In some embodiments, the method may include determining the probability of the at least event based on real-world clinical data.

BRIEF DESCRIPTION OF THE DRAWINGS

FIG. 17 depicts a table of exemplary avatars, a reference population, and comparator group characteristics.

FIG. 18 depicts exemplary erythropoiesis stimulating agents (ESA) and hemoglobin (Hgb) results for VIAT 1.0, VIAT 2.0, VIAT 3.0, and exemplary clinical data.

FIG. 19 depicts a table of exemplary ESA doses per category of average monthly hemoglobin.

FIG. 20 depicts a table of exemplary avatar patient characteristics.

DETAILED DESCRIPTION

Figure 1:
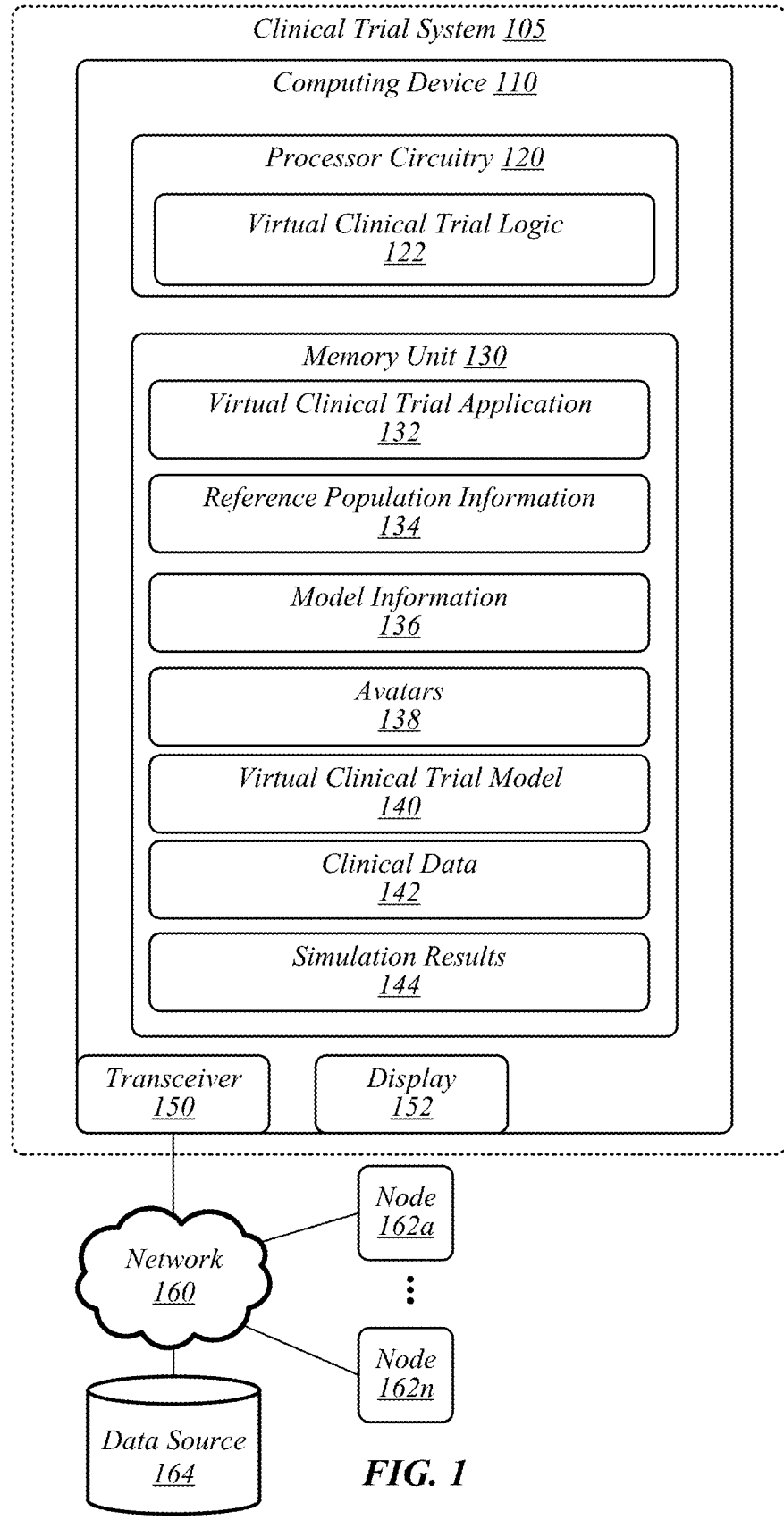
FIG. 1 illustrates an embodiment of a first operating environment.

Various embodiments may generally be directed toward systems, methods, and/or apparatuses for generating, performing, and/or evaluating in silico or virtual clinical trials (VCTs). In some embodiments, the VCTs may be configured to model a health condition of a population of patients. In some embodiments, VCTs may be or may include a virtual anemia trial (VIAT) operative for simulating anemia treatments. In some embodiments, VIATs may be operative for anemia treatments for dialysis patients, such as chronic hemodialysis (HD), peritoneal dialysis (PD) patients, and/or the like. In various embodiments, VIATs may be operative to evaluate virtual patients (or avatars) for various aspects of anemia treatments, such as hemoglobin levels, erythropoiesis levels, pharmaceutical treatment options, drug interactions, dialysis, and/or the like. In exemplary embodiments, the avatars may be configured to model or otherwise represent a health condition of a population of patients (for instance, a population of HD patients modeled based on historical clinical data).

In exemplary embodiments, a comprehensive physiology-based mathematical model of erythropoiesis and patient-level clinical data may be used to create a plurality of avatars based on real-world HD patients. An anemia protocol used in a large cohort of HD patients may be tested to create the avatars and then compared to the same tests conducted in avatars that were generated based on individual patient data routinely measured in HD patients. In exemplary embodiments, the anemia protocol may be or may include an erythropoiesis stimulating agent (ESA) treatment protocol. In some embodiments, clinic modules, such as stochastic modules, may be implemented in a VIAT, for example, to reflect the daily clinical routine and increase the ecological validity of the VIATs. In various embodiments, for example, individual hemoglobin (Hgb) levels and a corresponding anemia treatment may be simulated for a trial duration, such as an entire year. Results of VIATs configured according to some embodiments may be compared to real-world clinical data, for example, from a random comparator group sampled from a sufficiently large reference population of HD patients (for example, about 30,000 to 100,000 patients) who were treated for anemia using the same or substantially the same protocol.

To mitigate and overcome the challenges of human clinical trials, such as randomized clinical trials (RCTs), alternative trial strategies have been developed, such as adaptive design clinical trials. In silico or virtual trials (for instance, performed or performed substantially entirely on a computer) have been introduced to increase the repertoire of clinical trial designs. Realistic simulations of clinical trials can provide valuable information regarding safety and limitations of treatment protocols and have been shown to assist in the cost-effective planning of clinical studies.

However, conventional VCTs typically utilize Monte Carlo-type sampling (and re-sampling) techniques to create virtual patient populations. While conceptually functional, Monte Carlo simulations may fall short in representing the (patho)physiology of an actual individual subject because only population-derived estimates of patient characteristics may be represented. Furthermore, conventional VCTs often fail to represent operational processes and challenges in patient treatment centers, such as dialysis clinics, that have a material impact on VCT outcomes. Accordingly, evaluation of conventional VCTs (for instance, via comparison with actual clinical data corresponding to the VCT) typically demonstrates poor alignment with real-world results, therefore severely diminishing the value and predictive abilities of conventional VCTs.

Accordingly, some embodiments provide VCTs, such as VIATs, that integrate internal, external, and ecological validity. For example, various embodiments may provide model-based VCTs aimed at anemia treatment in hemodialysis (HD) patients. For example, VIATS configured according to some embodiments may simulate Hgb levels and subsequent anemia treatment on a per-patient basis over the course of a year for comparison to real-life clinical data of a relatively large population of HD patients (for example, about 80,000 HD patients). In this manner, VCTs operative according to some embodiments may provide improved external and ecological validity of a VCT, significantly increasing the clinical value based upon the predictive power of VCTs.

In various embodiments, VIATs may be formed based on a comprehensive physiology-based mathematical model describing the development of red blood cells (erythropoiesis) and the effect of erythropoiesis stimulating agents (ESA) on this process A non-limiting example of such a model may be or may be derived from a model as described in Fuertinger, D. H., Kappel, F., Thijssen, S., Levin, N. W. & Kotanko, P., "A Model of Erythropoiesis in Adults with Sufficient Iron Availability," J. Math. Biol. 66, 1209-1240 (2013), which is incorporated by reference herein. The use of physiology-based mathematical models in VIATs according to some embodiments may provide intrinsic internal validity, as well, as the causal relation between an intervention and the corresponding outcome is clearly defined and easily comprehensible. Further, by definition, a deterministic model design, such as the model designs used in VIATs according to some embodiments, may generate reproducible results so that a specific intervention always or substantially always results in the same outcome.

In some embodiments, advanced mathematical and computational techniques may be applied to create a large population (for example, greater than or equal to 5,000) of avatars of real HD patients receiving ESA treatment for anemia. Accordingly, VIATs operative according to some embodiments may be integrated into individual real-life clinical patient data in the modeling process to improve external validity. For example, in some embodiments, a plurality of sample patients may be selected from a reference population and one avatar may be created for each sampled patient.

In various embodiments, "clinic modules" (for example, informed by real-life operational data) may be incorporated or otherwise implemented in VCT designed to create an in silico test environment that reflects operational processes and challenges in dialysis clinics. In some embodiments, the clinic modules may be stochastic or stochastic-based. Clinic modules according to exemplary embodiments may include information on laboratory schedules and processing times, patient non-adherence, hospitalizations, and/or the like. In some embodiments, clinic modules may be operative to model operational aspects including real-world events, conditions, and/or the like that may have a material effect on the outcome of a clinical trial. Such real-world events, conditions, and/or the like are not taken into account in conventional VCTs, but, nonetheless, may have an effect on the outcome of a VCT and/or actual clinical trial (such as an RCT). In this manner, various embodiments may operate to generate clinical trial results with markedly improved and realistic emulation of real-world clinical trial conditions. Integration of clinic modules into VCTs may, among other things, enhance the ecological validity of a VCT. In some embodiments, VCT and/or VIAT results conducted on avatars utilizing clinic modules may be implemented to improve anemia therapy for real-world patients. In addition, by pre-selecting promising dosing strategies, the chance of a successful clinical trial can be increased and with the support of in silico results the size and/or duration of a subsequent trial might be decreased. Thus, a well-designed virtual clinical trial may shorten the time to assess improved and novel therapies and consequently may shorten the time to deployment of therapies in the clinical setting. Accordingly, systems, methods, and apparatuses according some embodiments may provide technological advantages over conventional systems, including improvements in computing technology. For example, VCT processes according to some embodiments may provide VCTs, such as VIATs, that have improved predictive capabilities (for instance, are better able to simulate real-world clinical trials) than conventional systems. As such, computing devices implementing VCTs and/or VIATs according to some embodiments may be able to provide users with more accurate results than conventional systems, which may allow users to achieve improved research results for pharmaceuticals, device design, treatment regimens, and/or the like and to develop improved therapies faster and with better accuracy.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In this Detailed Description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage clinical trials and information associated with clinical trials. In various embodiments, analysis system 105 may include computing device 110. Computing device 110 may include processing circuitry 120, a memory unit 130, a transceiver 150, and/or a display 152. Processing circuitry 120 may be communicatively coupled to memory unit 130, transceiver 150, and/or display 152.

In some embodiments, computing device 110 may be connected to network 160 through transceiver 150. Network 160 may include nodes 162a-n, for example, remote computing devices, data sources 164, and/or the like.

Processing circuitry 120 may include and/or may access various logic for performing processes according to some embodiments. For instance, processing circuitry 120 may include and/or may access virtual clinical trial logic 122. Processing circuitry and/or virtual clinical trial logic 122, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 2300 of FIG. 23. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although virtual clinical trial logic 122 is depicted in FIG. 1 as being within processing circuitry 120, embodiments are not so limited. For example, virtual clinical trial logic 122 may be located within an accelerator, a processor core, an interface, an individual processor die, implemented entirely as a software application (for instance, virtual clinical trial application 132) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a virtual clinical trial application 132 that may operate, alone or in combination with virtual clinical trial logic 122, to perform various functions for generating, performing, and/or evaluating VCTs according to some embodiments. In some embodiments, virtual clinical trial application 132 may include application programming interfaces (APIs) and/or graphical user interfaces (GUIs) to read, write, and/or otherwise access information, such as via display 152, web interfaces, mobile application ("mobile applications," "mobile apps," or "apps"), and/or the like. In this manner, in some embodiments, an operator may search, visualize, read, add to, or otherwise access information associated with generating, performing, and/or evaluating VCTs.

In some embodiments, memory unit 130 may store various information associated with generating, performing, and/or evaluating VCTs, including, without limitation, reference population information 134, model information 136, avatars 138, clinical data 140, simulation results 142, and/or the like. In some embodiments, information stored in memory unit 130 may be retrieved from and/or moved into a data source 164 including, without limitation, a hospital information management system (HIMS), laboratory information management system (LIMS), Health Information System (HIS), electronic medical records (EMR), a clinical trial database, and/or the like.

In various embodiments, virtual clinical trial application 132 (which may be or may be included within virtual clinical trial logic 122) may operate to generate, perform, and/or evaluate VCTs, including VIATs. In some embodiments, virtual clinical trial application 132 may access reference population information 134, for example, associated with a reference population of long-term HD patients. In various embodiments, the reference population information 134 may include personal information (for instance, age, gender, and/or the like), physical characteristics (for instance, height, weight, and/or the like), medical records, health history information (for instance, routinely-collected clinical information), and/or the like. Embodiments are not limited in this context.

Virtual clinical trial application 132 may generate avatars 138 based on the reference population information 134. For example, a group of individuals may be selected from the reference population associated with reference population information 134. In some embodiments, the group of individuals may be selected at random, selected based on various selection criteria specified in model information 136, and/or a combination thereof. In various embodiments, personalized avatars 138 may be generated using individual patient information from the reference population information 134.

In some embodiments, model information 136 may include information that may be used to generate virtual clinical trial models 140. In various embodiments, model information 136 may include selection criteria for patients that may be used as the basis for avatars 138, clinical model information, model parameters, machine learning models, and/or the like. In various embodiments, model information 136 may be or may include a template for building a virtual clinical trial model 140 by virtual clinical trial application 132.

In exemplary embodiments, virtual clinical trial application 132 may simulate (or "run") a virtual clinical trial model 140 to generate simulation results 144. In various embodiments, simulation results 144 may be compared, for instance, using various statistical methods, to real-world clinical data 142 to evaluate the effectiveness of a virtual clinical trial model 140. In various embodiments, clinical data 142 may include data from a large cohort of HD patients (for instance, greater than or equal to about 37,000 HD patients) over a baseline duration (for instance, a period of about 90 days). In general, the effectiveness of a virtual clinical trial model 140 may be evaluated based on the ability of the virtual clinical trial model 140 to simulate real-world conditions and/or predict real-world outcomes.

Figure 2:
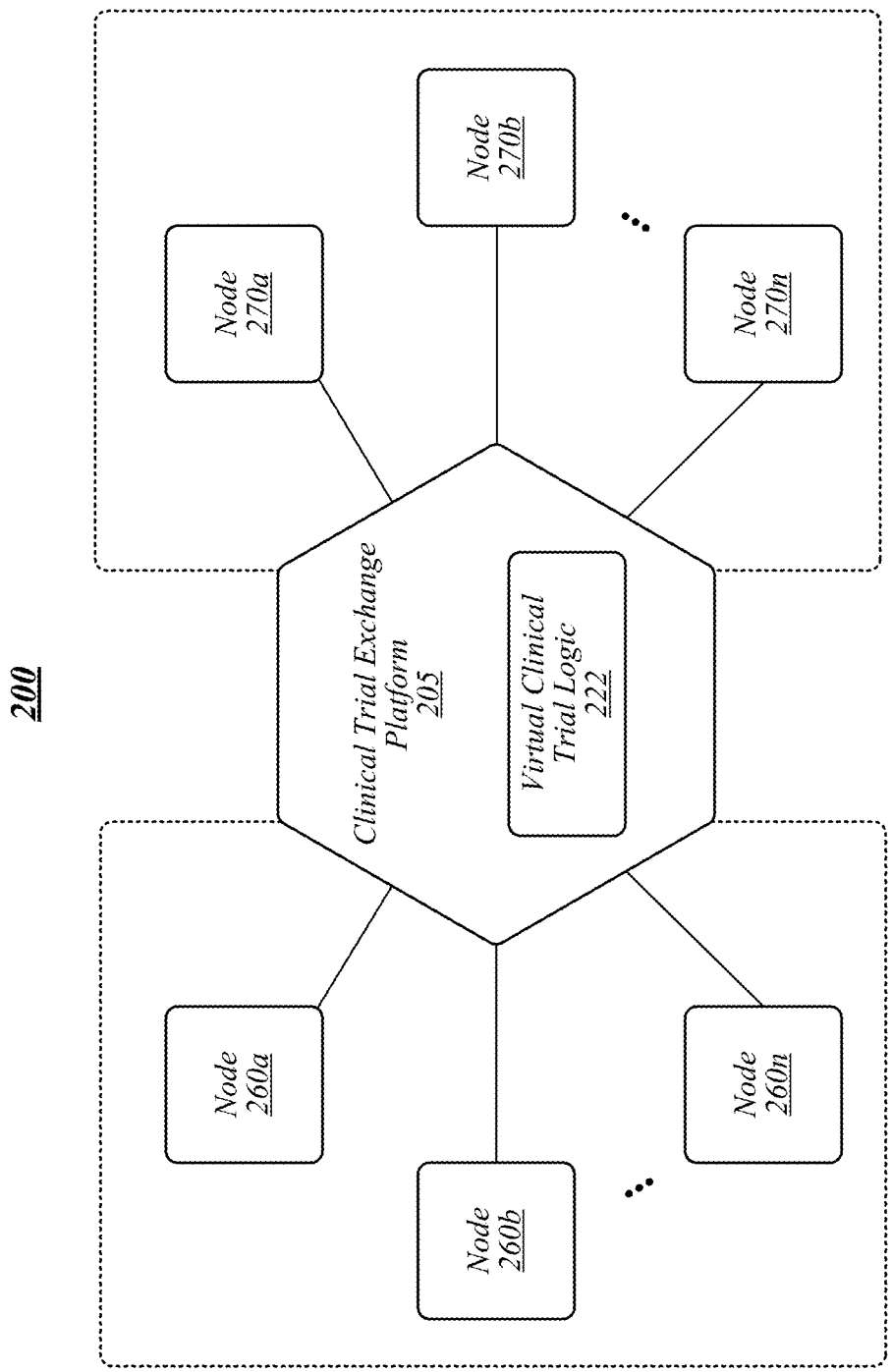
FIG. 2 illustrates an embodiment of a second operating environment.

FIG. 2 illustrates an example of an operating environment 200 that may be representative of some embodiments. As shown in FIG. 2, operating environment 200 may include an clinical trial exchange platform 205. In some embodiments, clinical trial exchange platform 205 may be operative to provide for the exchange of clinical data and/or clinical trial information (including VCTs and/or VIATS according to some embodiments) among interested entities. In various embodiments, clinical trial exchange platform 205 may include an application platform operative to provide data exchange services among nodes 260a-n and 270a-n. In exemplary embodiments, clinical trial exchange platform 205 may be a software platform, suite, set of protocols, and/or the like provided to customers by a manufacturer and/or developer ("developer") associated with medical devices, medical care services, clinical research services, laboratory services, clinical trial services, and/or the like.

For example, a developer may provide clinical trial exchange platform 205 as a data exchange interface for clinical trials to be used by researchers, government entities (for example, the FDA), and other stakeholders (for instance, pharmaceutical manufacturers, medical device manufacturers, and/or the like commissioning a VCT via a third party operating clinical trial exchange platform 205). An entity, such as a hospital, dialysis clinic, healthcare provider, government entity, regulatory entity, pharmaceutical manufacturer, medical device manufacturer, and/or the like providing and/or receiving clinical trial services via a node 270a-n provided by developer may use clinical trial exchange platform 205 to implement processes according to some embodiments. Other entities, may access clinical trial exchange platform 205 via a GUI, such as a client application, web interface, mobile app, and/or the like, to perform functions associated with virtual clinical trial logic 222. In some embodiments, at least a portion of clinical trial exchange platform 205 may be hosted in a cloud computing environment.

Nodes 270a-n may be data producers for virtual clinical trial logic 222 and nodes 260a-n may be data consumers of virtual clinical trial logic 222. For example, node 270a-n may include entities providing clinical data, model information, and/or the like used by virtual clinical trial logic 222 to generate, perform, and/or evaluate a VIAT. Nodes 260a-n may include third-party applications, decision makers, analysis processes, regulators, and/or other data consumers that may be interested in the results of generating, performing, and/or evaluating a VIAT. An entity may be both a data producer and a data consumer.

For example, node 260a may be a research organization contracted by a medical device manufacturer (node 260b) to perform clinical trials on a medical treatment regimen to obtain regulatory approval by a regulator (node 270a). Data producers 260a-n may provide analytical data, according to permissions, to analytical exchange platform 205, for example, in the form of records in a HIMS, LIMS, EMR, and/or the like. Data consumers 270a-n may access analytical data, according to permissions, via analytical exchange platform 205 (for example, through HIMS, LIMS, EMR, and/or the like and/or local copies of such records).

In some embodiments, clinical trial exchange platform 205 may operate according to a cloud-based model and/or an "as-a-Service" model. In this manner, clinical trial exchange platform 205 may provide for a service that operates as a single, central platform that allows entities to access clinical data, VIATs, model information, simulation results, and/or the like.

Figure 3:
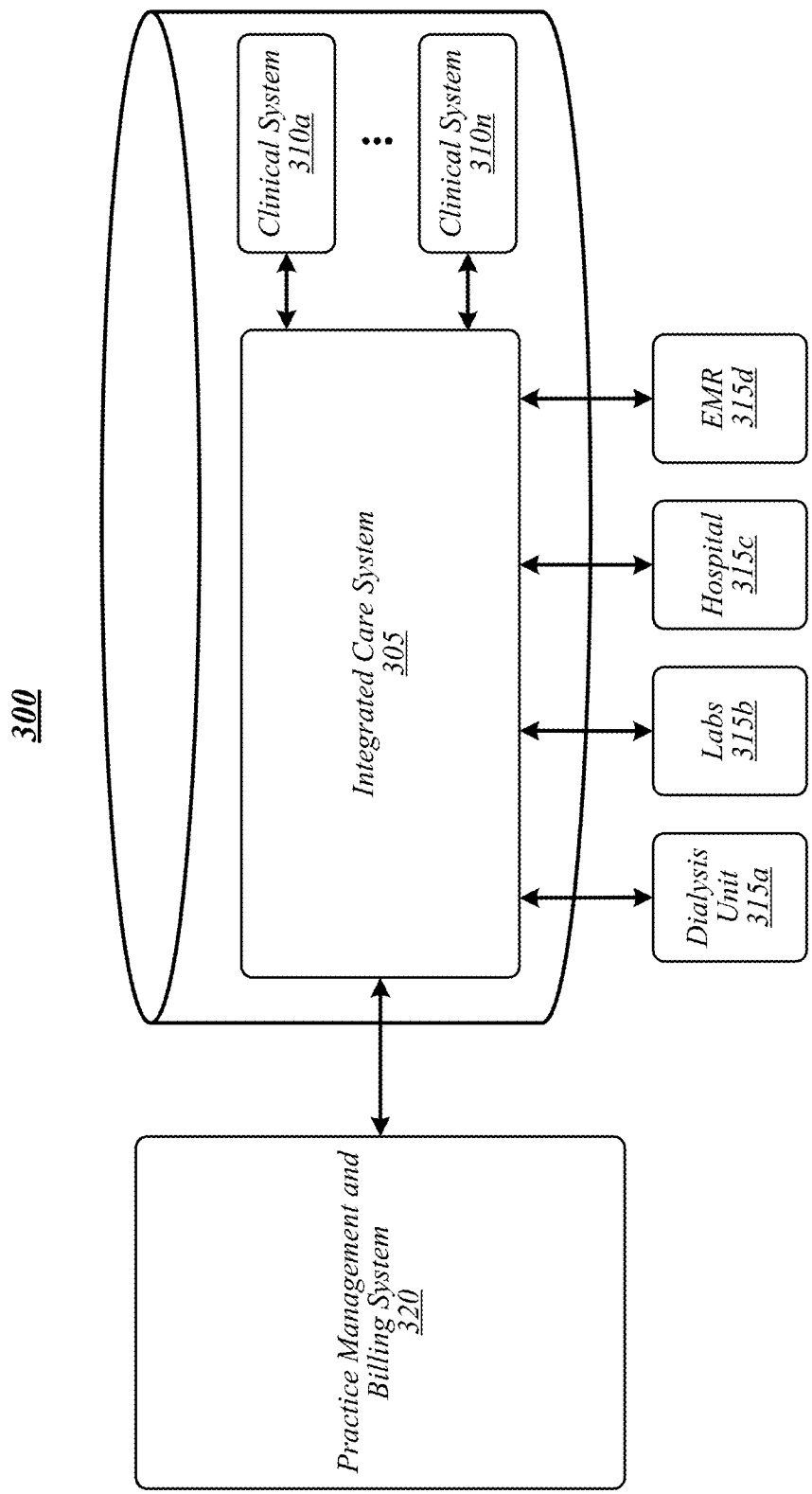
FIG. 3 illustrates an embodiment of a third operating environment.

FIG. 3 illustrates an example of an operating environment 300 that may be representative of some embodiments. As shown in FIG. 3, operating environment 300 may include an integrated care system 305 that may form a part of a clinical system for treating a patient in all aspects of care. In some embodiments, integrated care system 305 may include a specific implementation of clinical trial exchange platform 205.

Integrated care system 305 may be connectable to additional clinical systems 310a-n, including but not limited to a pharmacy, an End-Stage Renal Disease (ESRD) and/or Chronic Kidney Disease (CKD) data registry, a hospital, a dialysis clinic, a renal and/or kidney disease research facility, and/or the like. For example, integrated care system 305 may automatically send prescriptions and other patient information to a pharmacy based on information provided by a medical professional, and may be able to send and receive data and information to the CKD/ESRD data registry, for comparison to other patients and projections for future treatment. In another example, integrated care system 305 may determine and/or access information associated with a VIAT, such as clinical data and/or simulation results. Integrated care system 305 may determine events associated with CKD/ESRD and take appropriate action, including but not limited to informing patients, informing clinicians of when specific interventions are warranted, and/or alerting clinicians to upcoming important dates for interventions. In some embodiments, integrated care system 305 may determine such events based at least in part on information associated with VIATs, such as simulation results, clinical data, avatars, and/or the like.

One or more outside systems 315a-d may also be connectable to integrated care system 305. For example, outside systems 315a-d may include one or more of a dialysis unit (or dialysis machine) 315a, labs 315b, doctor's office and/or hospital 315c, and/or electronic medical records (EMR) 315d. Patient information may be sent and received between integrated care system 305 and the outside systems 315a-n, so that patient care and/or research may be more efficient, standardized, and consistent across several functions. For example, certain of the patient information may include information associated with one or more VIATs, such as outcomes for patients having characteristics associated with the patient. In another example, integrated care system 305 may receive information from a patient's electronic medical records, thereby accessing historical information. Dialysis unit 315a, labs 315b, doctor's office or hospital 315c, EMR 315d, and/or the like may send and receive information to and from integrated care system 305 based on patient treatment.

As described below with respect to FIGS. 21 and 22, in some embodiments, integrated care system 305 may provide information to a dialysis machine 2100 and/or 2200 for use in dialysis treatment. In some embodiments, integrated care system 305 may send the dialysis machine 2100 and/or 2200 a prescription from a medical professional for a prescribed dialysis treatment, in which case integrated care system 305 may receive the prescription from a doctor's office or hospital. Integrated care system 305 may also be able to verify the prescribed treatment against the patient's lab work or medical records. In exemplary embodiments, integrated care system 305 may remotely program the prescription onto the patient's dialysis machine and/or forward the prescription and/or measurement information to the machine for local set-up. In this manner, the patient may be sure to receive the necessary and correct treatment and may be prevented from administering or receiving an improper amount of dialysis treatment, thereby reducing human error and improving patient care. In various embodiments, at least a portion of the prescription may be based on a VIAT, such as simulation results associated with the patient or patient type (for instance, similar medical history, physical characteristics, treatment regimens, and/or the like).

Integrated care system 305 may also be able to inform the relevant medical professional based on information received from these outside systems 315a-n, as well as the additional clinical systems 310a-n, to provide appropriate medical treatment to the patient, including course(s) of treatment that may lessen or avoid negative outcomes, such as diminishing or completely eliminating a risk of hospitalization.

Figure 4:
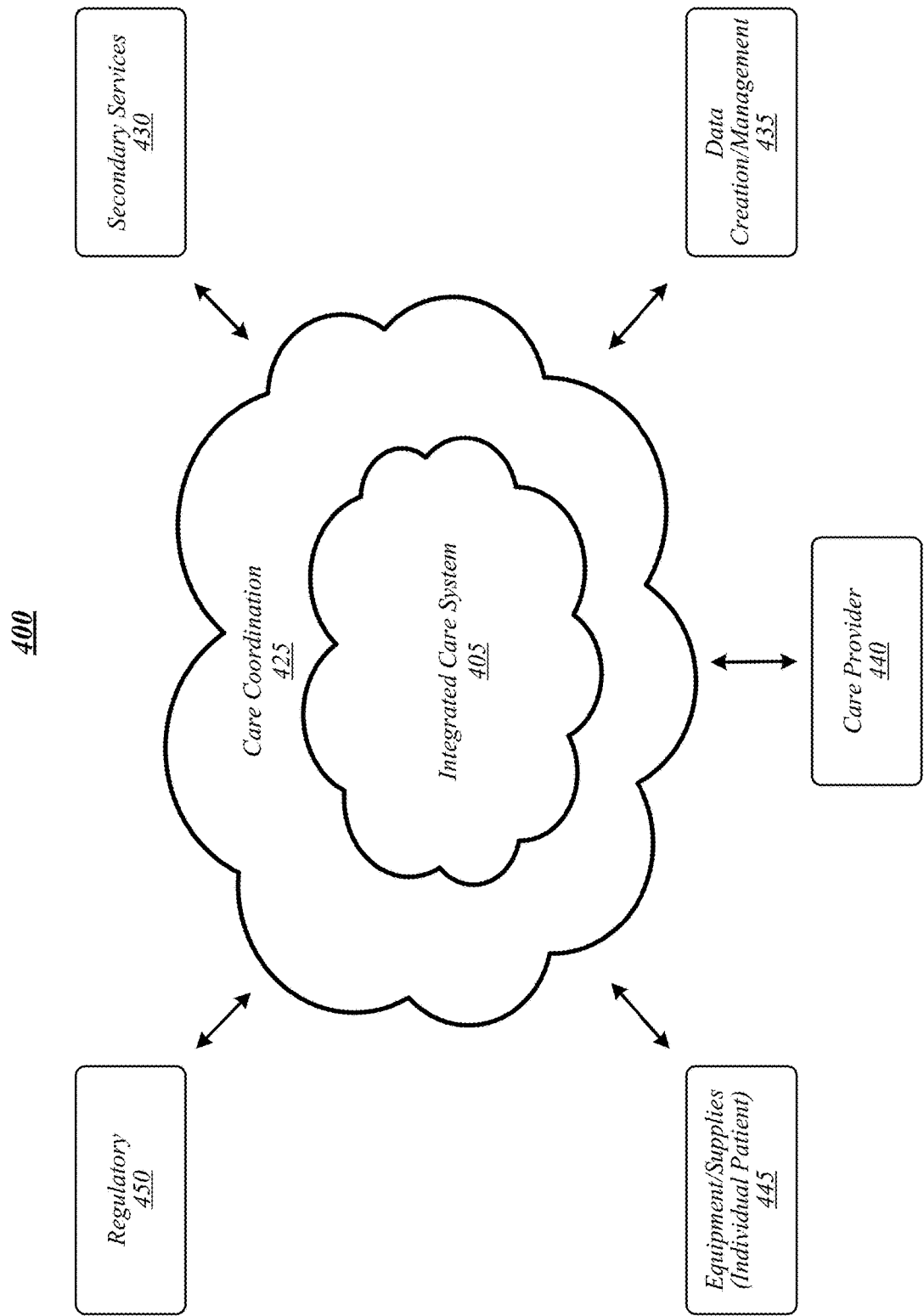
FIG. 4 illustrates an embodiment of a fourth operating environment.

FIG. 4 illustrates an example of an operating environment 400 that may be representative of some embodiments. As shown in FIG. 4, operating environment 400 may include a system of integrating patient care for use in treating kidney disease, for example, ESRD and/or CKD. In some embodiments, operating environment 400 may show additional details, including additional components and enumerations, and/or an expanded architecture, for example, of operating environment 300. For example, the population of patients diagnosed with ESRD have been increasing over time, often caused by several other diseases, including but not limited to diabetes, hypertension, and/or glomerulonephritis. Patients living with ESRD may face additional challenges due to the nature of the disease, for example, required lifestyle changes may lead to mental health deterioration. Additionally, at-home treatments may lead to increased isolation from medical professionals. As the healthcare landscape changes, opportunities to provide patients with resources for coordinating treatment may deliver additional patient health benefits beyond dialysis treatment.

In various embodiments, integrated care system 405 may integrate various healthcare models, for example, Accountable Care Organizations (ACO's), ESRD Seamless Care Organizations (ESCO's), Chronic Special Needs Plans (C-SNP's), and/or the like. Care coordination unit 425 may coordinate with integrated care system 405 to oversee and manage patient care. Various components may engage within integrated care system 405 to provide complete patient care via a care coordination unit 425. For example, any number of integrated care components may send and receive information to and from integrated care system 405, including but not limited to a secondary services component 430, a data creation and/or management component 435, a care provider component 440, an equipment and/or supplies component 445, a regulatory component 450, and/or the like Each component of an integrated care system 405 may include one or more units, including internal services and support as well as external services and support. In some embodiments, secondary services component 430 may include any number of services including, without limitation, laboratory services, personalized care services, clinical trial services, regulatory approval services, and/or pharmacy services. Each of secondary services 430 may send and receive patient information to integrated care system 405 for compilation and analysis. For example, a laboratory may automatically send results of patient bloodwork and other test results to integrated care system 405. Additionally, integrated care system 405 may automatically send testing instructions to the laboratory for selected tests on patient samples, based on determinations from medical professionals, and/or other information gathered by care coordination unit 425. Similarly, integrated care system 405 may automatically send prescriptions and dosage instructions to a pharmacy based on a patient's test results and other factors determined by integrated care system 405. The pharmacy may also send information to integrated care system 405 related to other patient prescriptions for potential adverse drug interactions, how timely a prescription is refilled, and/or patient interaction with the pharmacist, and/or the like. In some embodiments, a clinical trial service provider may send VIAT simulation and/or comparison results to integrated care system 405. In this manner, a service provider may determine a course of a clinical trial (for instance, a RCT) and/or treatment based on VIAT simulations.

Figure 5:
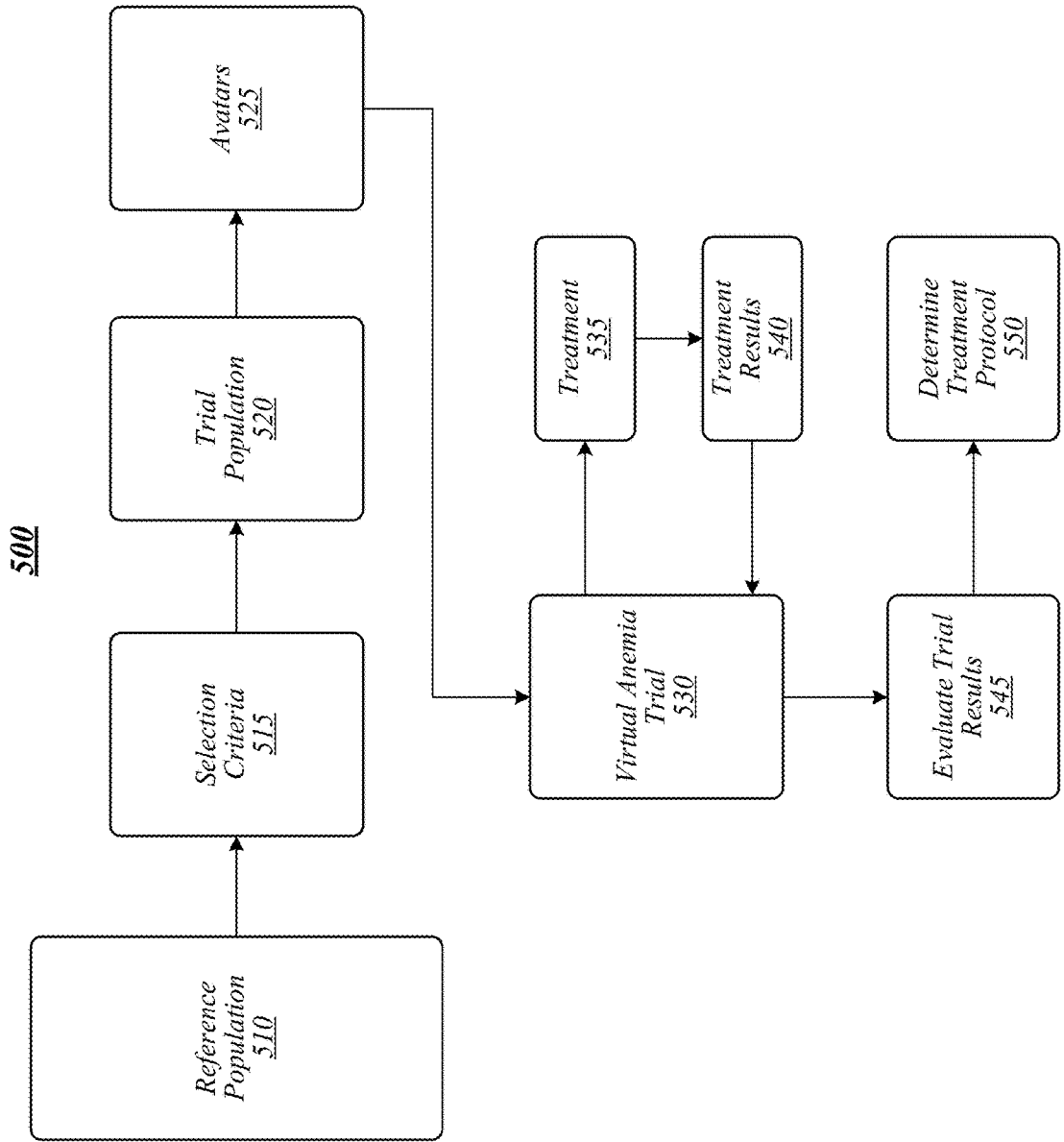
FIG. 5 illustrates an embodiment of a process flow according to some embodiments.

FIG. 5 illustrates a flowchart of an exemplary VIAT process 500 for implementing a VIAT according to some embodiments. In some embodiments, VIAT process 500 may include a process generated and/or performed by computing device 110, clinical trial exchange platform 205, and/or integrated care systems 305 and/or 405. Although VIAT process 500 depicts certain steps occurring in a specific sequence, embodiments are not so limited, as certain steps may be performed out of order or may not be performed in a particular implementation according to some embodiments.

At step 510, VIAT process 500 may access a reference population. In some embodiments, the reference population may include patients undergoing an anemia treatment protocol, HD patients undergoing an anemia treatment protocol, patients from a particular hospital system, treatment clinic system (for instance, the Fresenius Kidney Care (FKC) clinics operated by Fresenius Medical Care North America (FMCNA) of Waltham, Massachusetts), combinations thereof, and/or the like. In some embodiments, the reference population may include at least about 10,000 patients, about 20,000 patients, about 30,000 patients, about 40,000 patients, about 50,000 patients, about 80,000 patients, about 100,000 patients, about 200,000 patients, and any value or range between any of these values (including endpoints).

VIAT process 500 may determine selection criteria at step 515 for selecting a trial population. In some embodiments, the selection criteria may include random sampling criteria, such as Monte Carlo-based simulation criteria. In various embodiments, selection criteria may include specific selection parameters to filter the reference population to determine the trial population. Non-limiting examples of selection criterial may include age, disease state, risk factors, patient prescription regimine, dialysis treatment regimen, duration of treatment information, duration of medical information, and/or the like. For example, patients may be included in the trial population if they were above 18 years of age, received at least one administration of methoxy polyethylene glycol-epoetin beta (for example Mircera produced by Roche Holding AG of Basel, Switzerland) during a first specific time period and had clinical routine laboratory data for at least 4 months during a second specific time period. In another example, patients may be excluded if they received any other ESA after their first administration of methoxy polyethylene glycol-epoetin beta, if a patient had ICD 9 codes in their electronic health record that indicated an increased risk for bleedings (for instance, patients with gastric ulcers, esophageal varices, colon polyps, etc.), and/or the like.

At step 515, VIAT process 500 may generate a sample population based on the selection criteria according to some embodiments. In some embodiments, the sample population may include at least about 1,000 patients, about 2,000 patients, about 3,000 patients, about 4,000 patients, about 5,000 patients, about 8,000 patients, about 10,000 patients, about 20,000 patients, and any value or range between any of these values (including endpoints). In some embodiments, the trial population may include patients typically excluded from conventional clinical trials, such as elderly, frail, and multimorbid patients.

VIAT process 500 may generate avatars at step 525. In general, an avatar (or virtual patient) may include a mathematical model configured to represent a patient and/or physiological systems or subsystems thereof. In some embodiments, each avatar may be or may include various data structures, inputs, outputs, data (for instance, patient data), models (for instance, disease models, treatment models, pharmaceutical interaction modules, and/or the like), and/or the like. For example, an avatar may have an input for a prescription for drug A and a corresponding model for a patient taking drug A according to the prescription (for instance, modeling the effect on Hgb levels for drug A). In another example, the model (for instance, via a clinical model according to some embodiments) may take into account a patient not following the prescription (for instance, only taking drug A 80% of the times required by the prescription) and/or other behavioral aspects of the avatar. The avatar may have a corresponding output, such as the results of taking drug A (for instance, predicted Hgb levels).

In some embodiments, personalized avatars may be generated for each individual patient of the sample population. In various embodiments, the number of avatars may be about 1,000, about 2,000, about 5,000, about 10,000, about 20,000, and any value or range between any of these values (including endpoints). Avatars may be associated with various characteristics, including, without limitation, age, gender, race, body mass index, vintage, comorbid diabetes, hemoglobin, pre- and post-treatment weight, pre- and post-treatment systolic blood pressure, treatment time, ultrafiltration (UF) volume, interdialytic weight, albumin, iron dose, dialysate sodium, neutrophils to lymphocytes ratio, transferring saturation, and/or the like.

In various embodiments, a population of avatars may be generated by sampling parameter values from a defined parameter space. In some embodiments, the parameter distributions may be used to describe a physiologically reasonable parameter space meaningful for HD patients. In exemplary embodiments, the avatars may be generated using data obtained from real-world patients, including, for example, routinely collected clinical data from individual HD patients treated for anemia. In some embodiments, the clinical data used to generate avatars may include data over a baseline time period, such as 30 days, 60 days, 90 days, 120 days, 6 months, a year, and values or a range between any two of these values (including endpoints).

In some embodiments, stimulus-response constraints may be defined for the avatar for each patient using their individual clinical data (e.g., in the example case, data on anemia treatment). Model parameters to generate the avatars may be selected for each patient from a pre-defined set of meaningful clinical parameters. Non-limiting examples of parameters may include disease state, Hgb levels, drug and/or treatment responsiveness (for instance, a parameter may be set from a minimum value to a maximum value indicating how a patient improves or does not improve in response to receiving a drug or other treatment), parameters associated with anemia treatment, parameters associated with ESA therapy, and/or the like. In various embodiments, parameter values that explain the pharmacodynamical response to ESA therapy for a specific patient within a pre-defined accuracy may represent a patient-specific unique avatar. Embodiments are not limited in this context.

At step 530, VIAT processes may implement a VIAT according to some embodiments. In some embodiments, the VIAT may include a comprehensive physiology-based mathematical model of treatment methods. For example, the VIAT may perform virtual treatment methods on the population of avatars to generate treatment results, such as Hgb levels of patients following a round of virtual treatment. In another example, the VIAT may operate a model emulating the development of red blood cells (erythropoiesis) and the effect of ESA on this process. In various embodiments, the VIAT may include improved intrinsic internal validity over conventional processes, for example, as the causal relation between an intervention and the corresponding outcome may be more clearly defined and easily comprehensible. Further, by definition, a deterministic model design, such as the one used in the VIAT, generates reproducible results so that a specific intervention may always result in the same outcome.

In some embodiments, the VIAT process 500 may include repeatedly performing treatments on the avatars at step 535 and determining treatment results at step 540. For example, individual Hgb levels and the corresponding anemia treatment may be simulated over a duration, such as over a period of a year. In another example, for each avatar, weekly Hgb values may be simulated and decisions on ESA dose adjustments may be made following an anemia treatment. In some embodiments, a VIAT may be modeled to follow a specific treatment protocol, such as a protocol used and/or proposed by a specific clinic, hospital, doctor, researcher, and/or the like.

In various embodiments, a VIAT may include clinic modules. In some embodiments, the clinic modules in the simulation may be operated to increase ecological validity (see, for example, FIG. 6). In various embodiments, the clinic modules may be of a stochastic nature and reflect important aspects of clinical routine. As described in further detail herein, the use of clinic modules are operable to improve the predictive ability of VIATs according to some embodiments.

Figure 6:
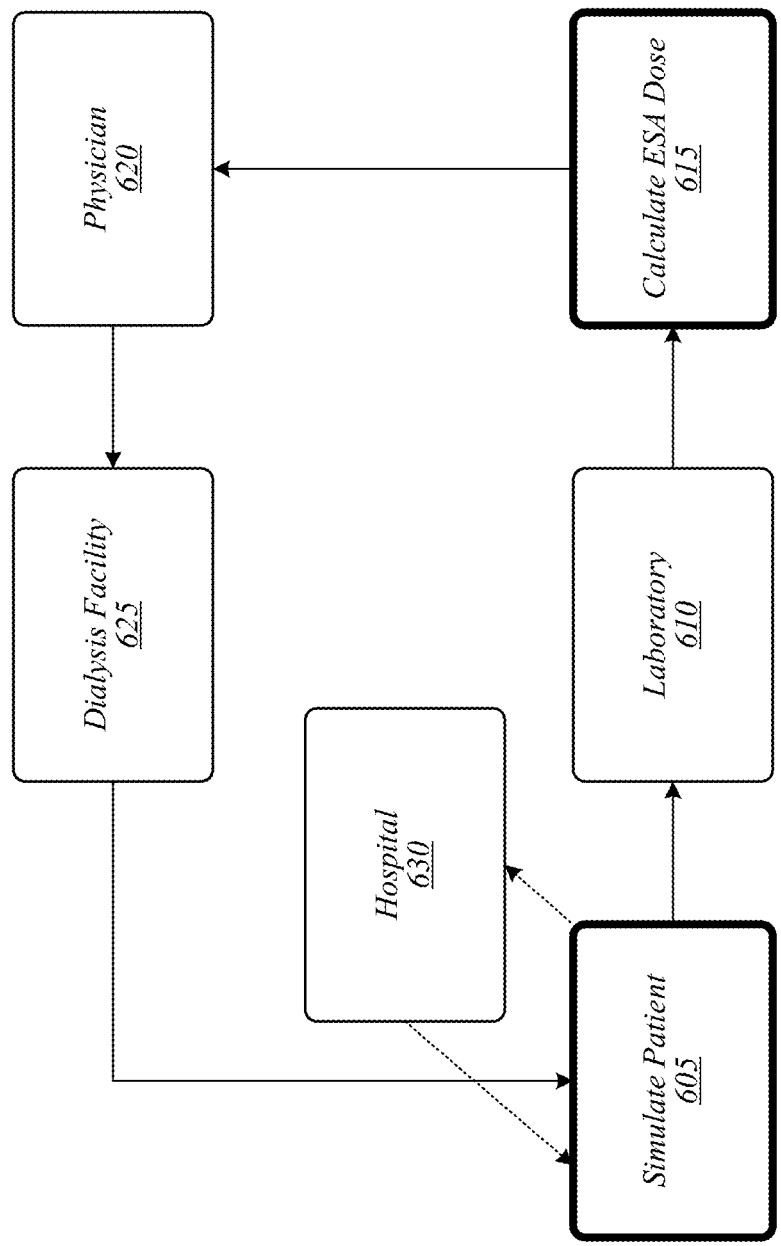
FIG. 6 illustrates clinic modules according to some embodiments.

Referring to FIG. 6, therein are depicted clinic modules according to some embodiments. In some embodiments, the clinic modules may be configured based on real-world operational data, such as operational data of a clinic, hospital, lab, and/or the like. In various embodiments, the clinic modules may be configured to create an in silico test environment that reflects operational processes and challenges in dialysis clinics. For example, the clinic modules may include information on laboratory schedules and processing times (for instance, long-distance shipping of blood samples), patient non-adherence, and hospitalizations, and/or the like. Embodiments are not limited in this context.

As shown in FIG. 6, clinic modules may include simulated patient 605, laboratory 610, calculated ESA dose 615, physician 620, dialysis facility 625, and/or hospital. In general, a clinic module may be configured to introduce factors into the VIAT simulation that may not be captured by clinical data or conventional modeling parameters. For example, a clinic module may introduce real-world events, tendencies, effects, influences, conditions, and/or the like that may have an impact on the VIAT results. In some embodiments, certain of the clinic modules may be deterministic, such as clinic modules 605 and 615, while others may be stochastic, such as clinic modules 610, 620, 625, and 630.

In some embodiments, laboratory module 610 may be included to introduce effects of a laboratory in the treatment process. In various embodiments, laboratory module 610 may include instrument operation, patient fluid status, sample handling, and/or the like. For example, laboratory module may add noise patterns to simulated Hgb levels to reflect both the measurement noise of the laboratory device and the varying fluid status of the patient, and/or may add shipment delays of blood samples, to account for the fact that a small fraction of blood samples that arrive at a laboratory may be unusable, and/or the like. Accordingly, a VIAT according to some embodiments may model real-world laboratories, which may generate errors, provide incomplete data, miss deadlines, and/or the like. Clinic modules 605-630 may be designed by analyzing the real-world challenges and using actual real-life data, for example, from a treatment system, physicians, and/or the like to determine probability estimates for treatment effects, such as hospitalization patterns, laboratory processing times, patient non-adherence, and/or the like.

In some embodiments, one or more of clinic modules 605-630 may include certain events, such as measurement errors (or noise), patient non-adherence (for instance, to treatment protocol, physician instructions, and/or the like), patient non-attendance for treatment for reasons other than hospitalization, patient non-attendance due to hospitalization, shipping schedules of blood samples and processing time, occurrence of unusable blood samples, common physician decisions (for instance, prescription of blood transfusions at very low Hgb), hospitalization frequency and duration, and/or the like. In various embodiments, the events may be configured to simulate real-world operational aspects of VIAT entities (for instance, hospitals, clinics, physicians, patients, and/or the like). In some embodiments, clinic modules 605-630 may include probabilities for each event associated therewith. In various embodiments, clinic modules 605-630 may include consequences for an event, such as missing a treatment if hospitalized. Accordingly, as an avatar (or the virtual information of an avatar, such as a virtual blood sample of the avatar) progresses through the clinic modules of the VIAT as depicted in FIG. 6, the VIAT may determine whether certain events have occurred (such as hospitalization, sample analysis noise and/or error, atypical and/or erroneous physician decision), and the results may be included in the VIAT. Accordingly, an avatar may proceed through the VIAT in a more realistic manner than in conventional systems. In this manner, a VIAT operative according to some embodiments may be more accurate and, for example, demonstrate improved ecological validity, therefore improving the value and predictive ability of the VIAT.

In some embodiments, the clinic modules 605-630 may be configured for performance of a VIAT. For example, each clinic module 605-630 may include a set of events, with each event associated with one or more trial elements, one or more probabilities, one or more event results, and/or the like. Each event may be configured to model an operational aspect of an entity, such as operational aspects of a clinic, patient, hospital, laboratory. In some embodiments, an operational aspect may include an operation, interaction, and/or the like of an entity within the clinical trial. For example, each entity may be associated with one or more operational aspects, such as sample handling and/or testing for a laboratory, evaluation and/or treatment for a physician, adhering to treatment for a patient, and/or the like. In various embodiments, an operational aspect may be associated with one or more events. For example, for a sample testing operational aspect of a laboratory, an event may include generating valid data, generating erroneous data, missing data, and/or the like. Embodiments are not limited in this context. In some embodiments, each clinic module 605-630 may include a set of default events. In various embodiments, a developer may generate a new event and specify the corresponding one or more trial elements, one or more probabilities, one or more event results, and/or the like. In exemplary embodiments, a developer may generate a new clinic module (for instance, a research institute clinic module) with a set of default events.

In some embodiments, a trial element of an event may include a characteristic of a VIAT associated with the event, such as a drug prescription, treatment, laboratory, physician, and/or the like. For example, in the VIAT, a patient may have a drug prescription trial element relating to a prescription of a drug as an operational aspect associated with a course of treatment. The event may include a prescription non-adherence event associated with the avatar not adhering to an aspect of the prescription (for instance, timing of taking the drug, incorrect dosage, missing doses, and/or the like). The probability associated with the event may be configured to indicate a frequency or probability of non-adherence for the avatar population (for instance, 10% of the population will not adhere to a prescription) and/or for a particular personal avatar (for instance, the avatar will not adhere to the prescription 10% of the time due to skipping a dose). The result may be configured to provide a result for the event (for instance, Hgb levels in the patient will be 10% lower than for a corresponding patient that did adhere to the prescription).

Referring to FIG. 5, VIAT process 500 may evaluate trial results at step 545. For example, the trial results obtained at step 540 may be compared to real-world clinical data, such as a corresponding comparator group (see, for example, Table 1 of FIG. 17). For example, ESA doses for the avatars from a VIAT may be compared to the actual doses of the real-world clinical data. In another example, physiological characteristics of avatars, such as Hgb values, may be compared to corresponding clinical data. Embodiments are not limited in this context. VIAT process 500 may determine a treatment protocol at step 550. For example, VIAT process 500 may determine new and/or improved treatment protocols for treating anemia based upon the results of the simulation performed by VIAT process 500. For example, the treatment results of a VIAT according to some embodiments may demonstrate that a pharmaceutical dosage in combination with a particular frequency of physician visits and/or treatment regimen may show improved results.

Experiments: VIATS of HD Patient Populations Undergoing Anemia Treatment

Three VIAT experiments were performed using different VIAT processes, termed VIAT 1.0, VIAT 2.0, and VIAT 3.0. The VIAT 3.0 used clinic modules according to some embodiments.

In order to alleviate statistical problems related to sample size differences between Avatars and the HD patient reference population, a comparator group of 6,659 individuals was selected from the reference population. Hence, performance assessments of the anemia protocol were based on equally-sized populations. Table 1 of FIG. 17 shows descriptive baseline characteristics of the reference patient population, the comparator group (subgroup of the reference population), and the avatar population. All three groups were balanced with respect to their clinical and laboratory data. Differences between the groups were that the avatar population was slightly younger (mean age 64.1 years vs. 65.6 years in the reference population), had been on dialysis longer (median vintage 3.4 years vs 2.3 years in the reference population), and the number of white HD patients were fewer in the avatar group (57% vs. 61% in the reference population).

Figure 7:
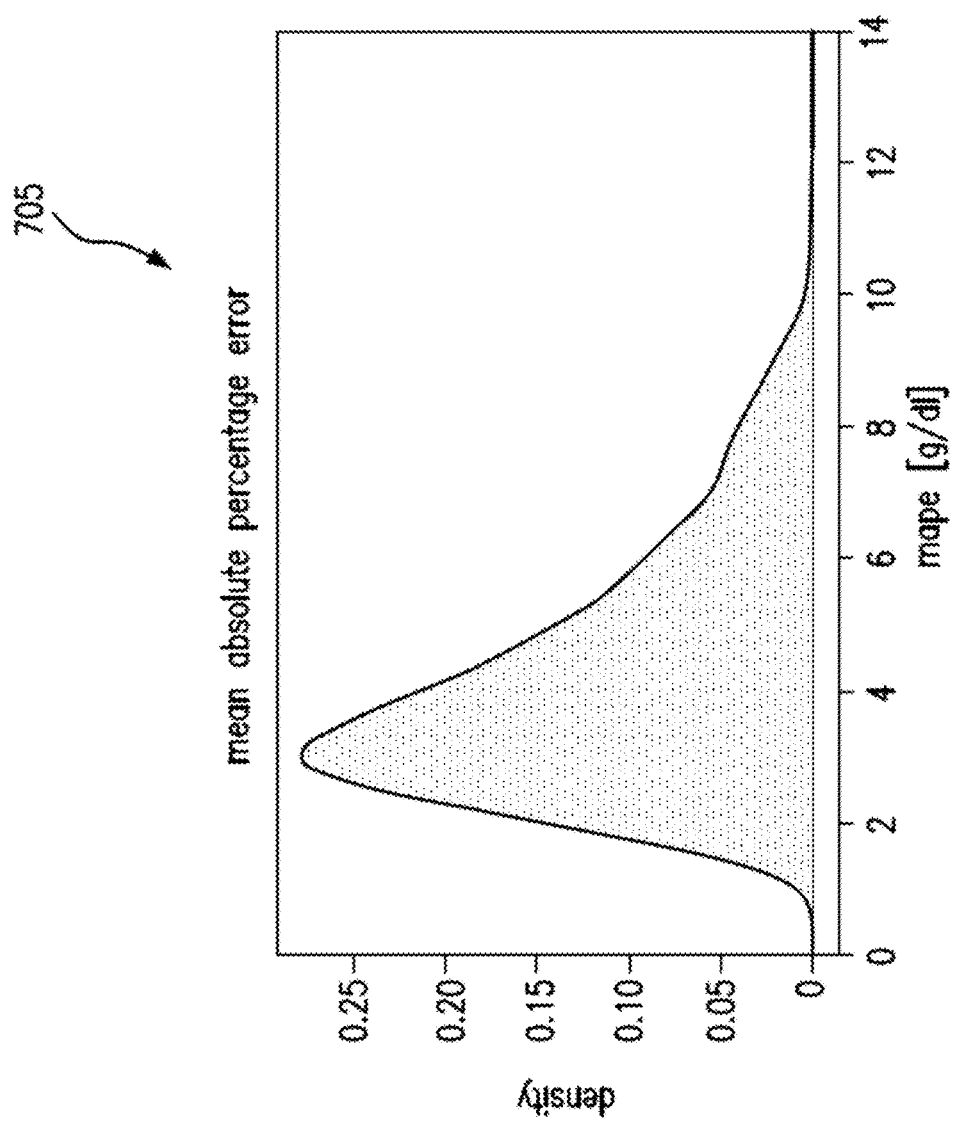
FIG. 7 a graph of an exemplary mean absolute percentage error (MAPE) between model simulation and empirical data.

Personalized anemia avatars were created using individual patient data. The model fit for individual patients was of excellent quality. FIG. 7 illustrates a graph of the mean absolute percentage error (MAPE) between model simulation and empirical data from the avatar patients showing a median value of 3.8% (range: 0.9% to 13.7%). While the distribution of the model error was subtly right-skewed, the MAPE was below 6.9% for 90 percent of the patients. All model parameters that were determined for individual patients were physiologically reasonable for HD patients.

A large population (for example, about 6,659) of avatars of real-life hemodialysis (HD) patients receiving ESA treatment for anemia was created. To that end, several parameters in a comprehensive physiology based mathematical model of erythropoiesis were adjusted using individual routinely collected clinical data. Patients were randomly sampled from a nationally representative United States HD population comprising over 37,000 individuals ("possible Avatar pool") to create the avatars. Stimulus-response constraints were defined for the model for each patient using their individual clinical data on anemia treatment. Model parameters were selected for each patient from a pre-defined set of meaningful clinical parameters. Parameter values that explained the pharmacodynamical response to ESA therapy for a specific patient within a pre-defined accuracy represent a patient-specific unique avatar.

Routinely collected data from Fresenius Kidney Care (FKC) clinics between December 2014 and February 2016 was used for avatar creation. Patients had to be older than 18 years, have received at least 1 ESA (Mircera) administration and were required to have a data record of at least 90 days. Anthropometric data (gender, height, weight, and/or the like), laboratory hemoglobin (Hgb) values and prescribed ESA administration over a training period of 90 days were used for the model adaptation. Patients that received an ESA other than Mircera during the training period were excluded. Further, patients with ICD 9 codes in their electronic health record that indicated an increased risk for bleedings (for example, patients with gastric ulcers, esophageal varices, colon polyps, and/or the like) were omitted.

The training period for an individual patient was defined to start with a routine laboratory Hgb measurement and end at the date of the first laboratory Hgb measurement after a period of at least 90 days. Patients that switched from a different ESA to Mircera began the training period after a 30-day interval starting from their last non-Mircera administration.

To generate the models, physiology-based mathematical models for erythropoiesis were used and adapted to individual HD patients using parameter estimation techniques by adjusting a small number of clinically relevant parameters. Gender, height and (average) post-dialytic weight of the patient was used to estimate post-dialytic blood volume using the Nadler formula. The number of stem cells committing to the erythroid lineage was adjusted based on the patient's blood volume and a steady state assumption for the model. The following model parameters were set on a per patient basis: RBC Lifespan, endogenous erythropoietin levels, half-life of administered ESA, and the slopes of the functions describing apoptosis of hematopoietic colony forming units and maturation velocity of bone marrow reticulocytes.

Model parameters were adjusted by randomly sampling 100,000 parameter values from the parameter distributions reasonable in HD patients. This created a coarse grid representing a non-uniform discretization of the five-dimensional parameter space. Simulations were generated for each patient by iteratively running the model across the sampled parameter space until pre-defined stopping criteria were met. A new grid of parameter vectors was generated after 2000 patients had been simulated. Criteria that needed to be met to accept a parameter set were defined as follows: The model prediction needed to be within the precision of the laboratory measurement method (measured value±2*standard deviation) after 60 and 90 days. The overall mean absolute error between data and model needed to be less than 1 g/dl. The first parameter vector that met both criteria was considered representative of the clinical characteristics underlying the specific patient and added to the Avatar population. Results of virtual clinical trials were compared to data from 79,426 HD patients in Fresenius Kidney Care (FKC) clinics between September 2015 and August 2016. In these clinics use of the tested anemia treatment protocol was part of standard care.

Figure 8:
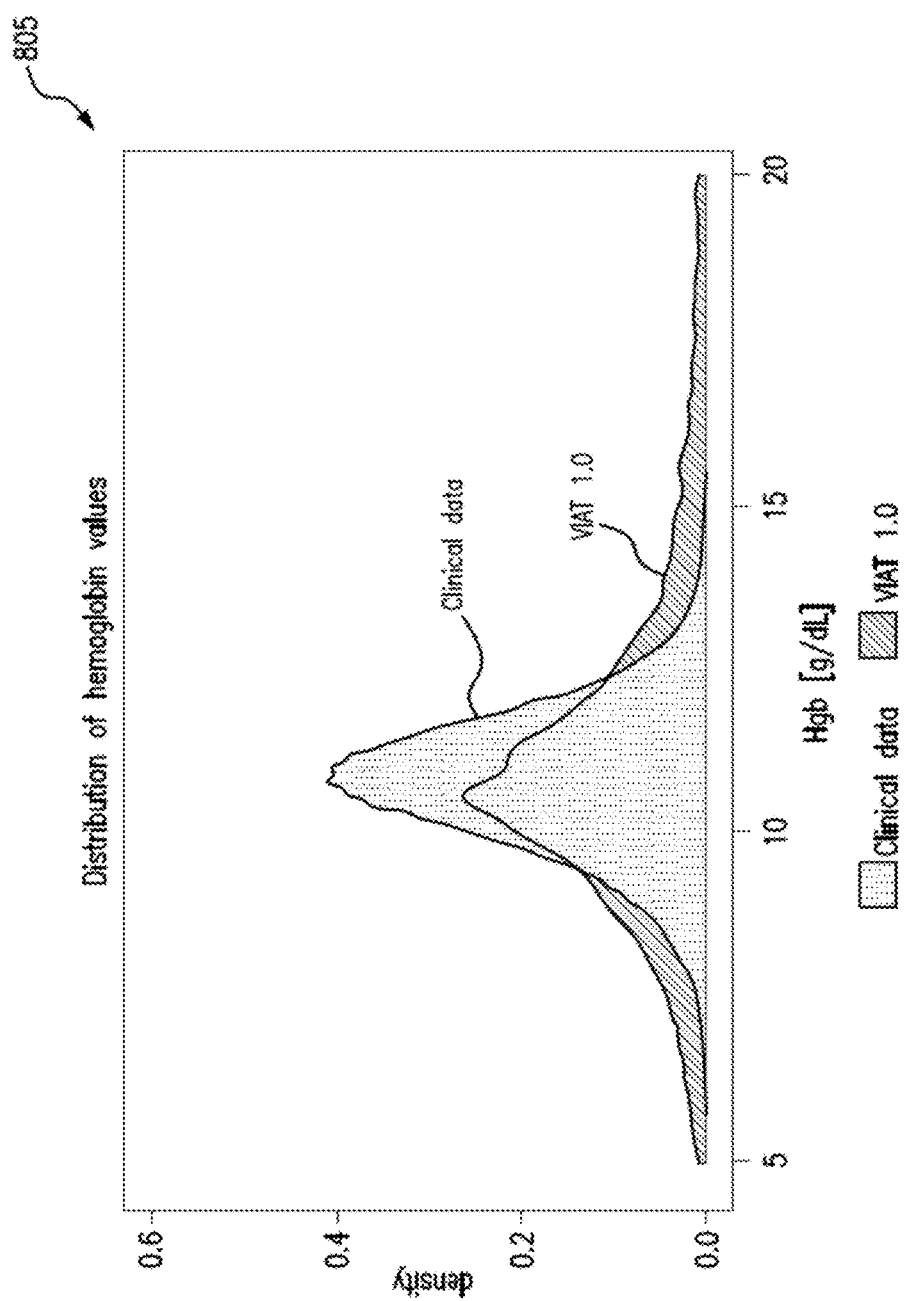
FIGS. 8-10 illustrate graphs of exemplary comparative results of an experimental virtual anemia trial (VIAT) 1.0.
Figure 9:
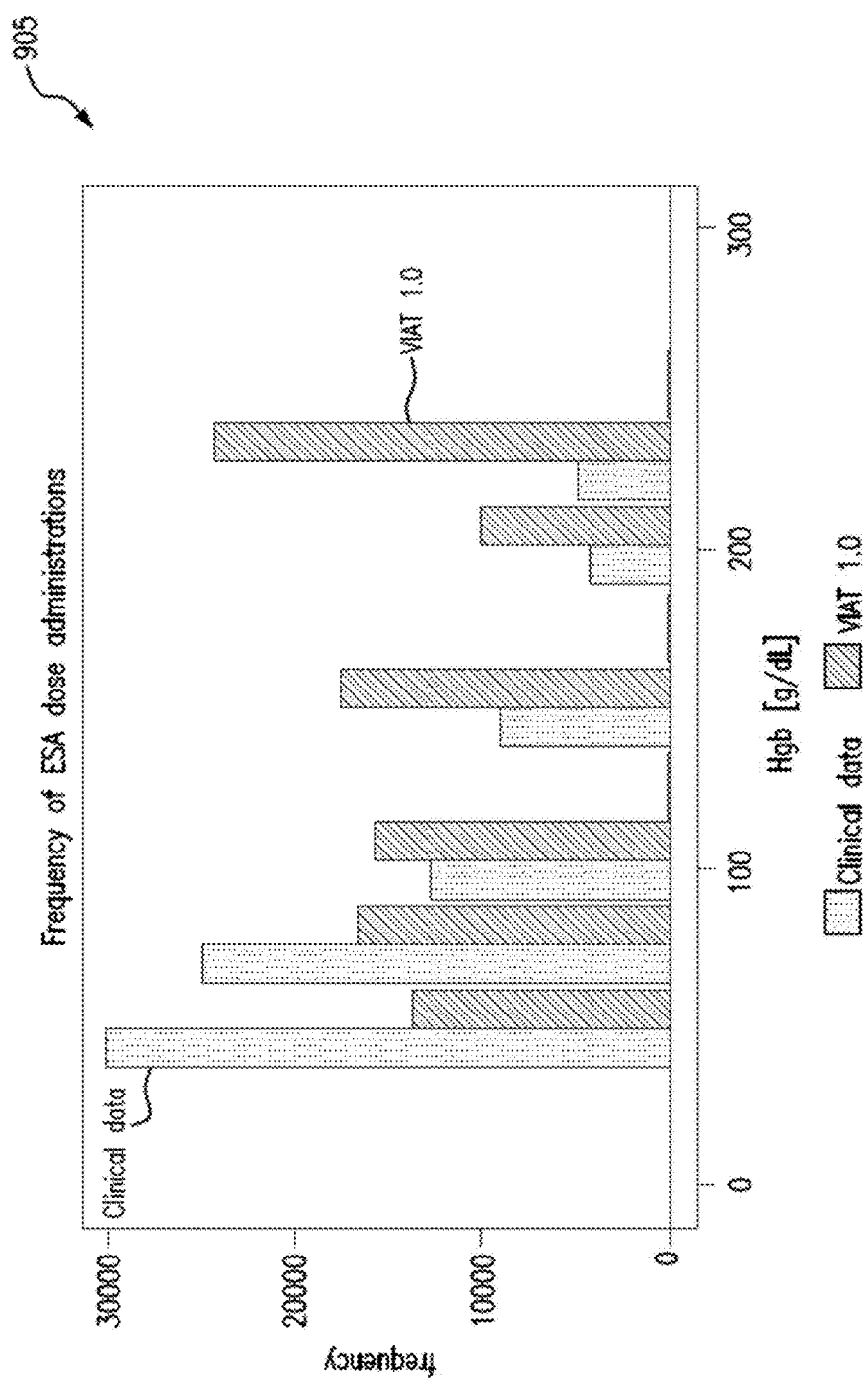
Figure 10:
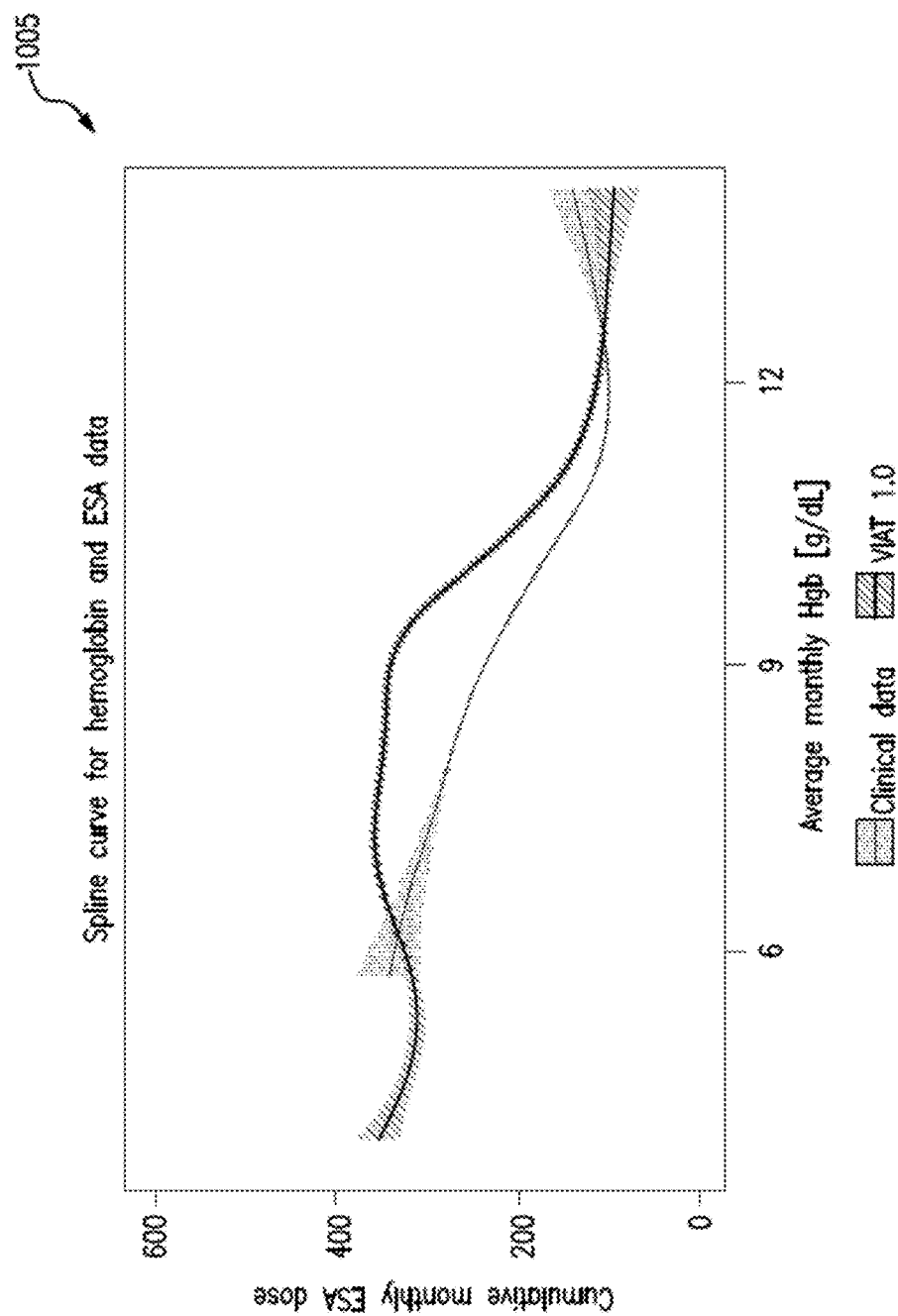

VIAT 1.0 involved using avatars created by Monte Carlo sampling. For VIAT 1.0, a cohort of 6,659 avatars was created by randomly sampling unique parameter values from a parameter space defined a priori. The parameter distributions used to describe the physiologically reasonable parameter space included parameters meaningful for HD patients. For each virtual patient, weekly Hgb values were simulated and decisions on ESA dose adjustments were made following an anemia treatment protocol used in a large number of U.S. dialysis clinics. FIG. 8 depicts a graph 805 of results of VIAT 1.0. As shown in FIG. 8, the results showed relatively poor alignment with certain aspects of the respective clinical data. The distributions of the predicted Hgb values (mean±standard deviation: 11.3±3.4 g/dl) did not reflect the empirical Hgb data (10.8±1.1 g/dl), as also demonstrated by Table 2 of FIG. 18. Moreover, the clinically prescribed ESA doses and the simulated prescribed doses showed an almost inverse pattern as depicted in graph 905 of FIG. 9. While the lowest ESA dose was the one most commonly administered in the real clinics, the simulation predicted that the highest dose would be applied most often. This behavior resulted in a 52.5% overestimation of ESA use per patient-year in the VIAT 1.0 compared to the clinical data. FIG. 10 depicts a spline curve for VIAT 1.0.

Figure 11:
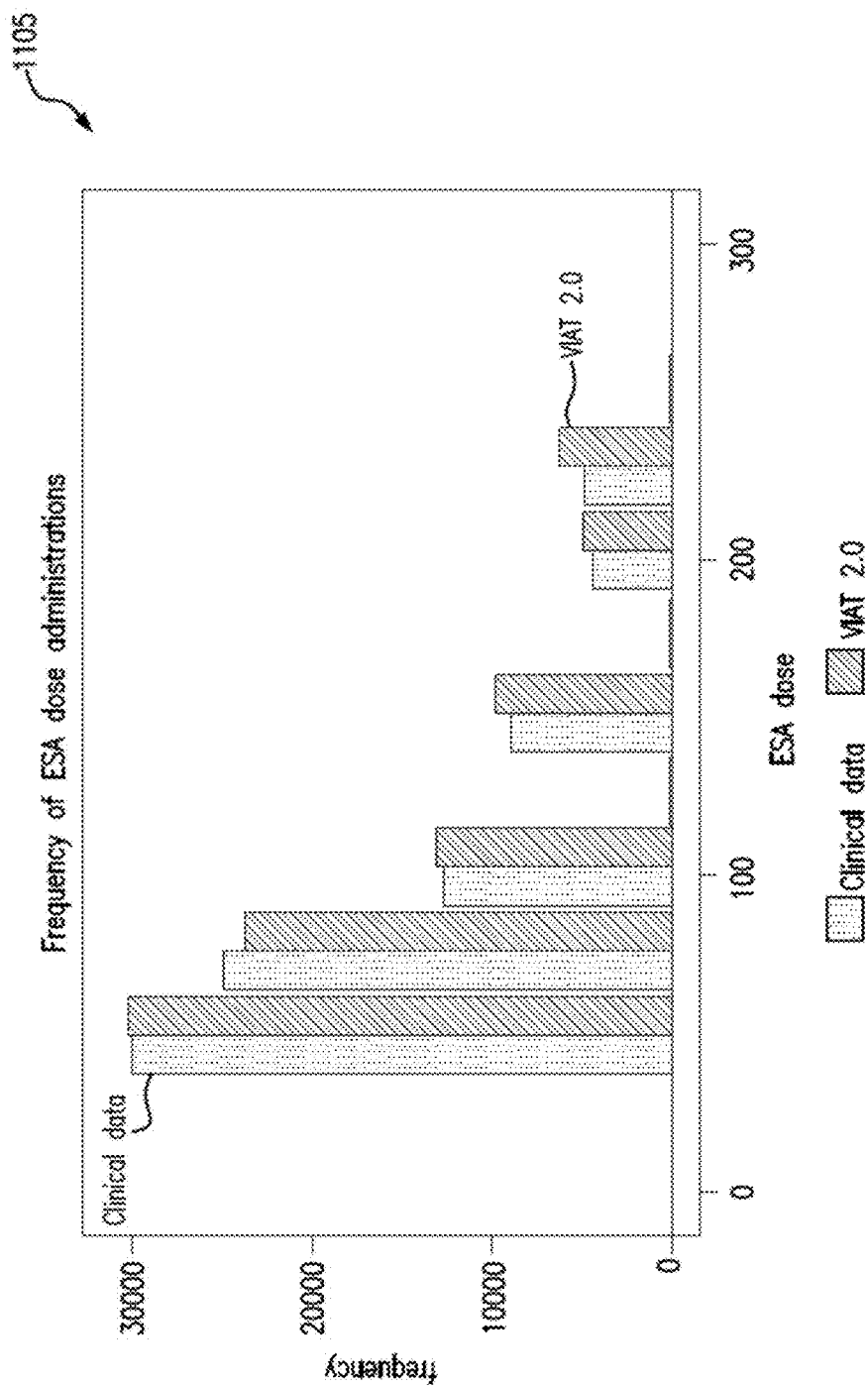
FIGS. 11-13 illustrate graphs of exemplary comparative results of an experimental VIAT 2.0.
Figure 12:
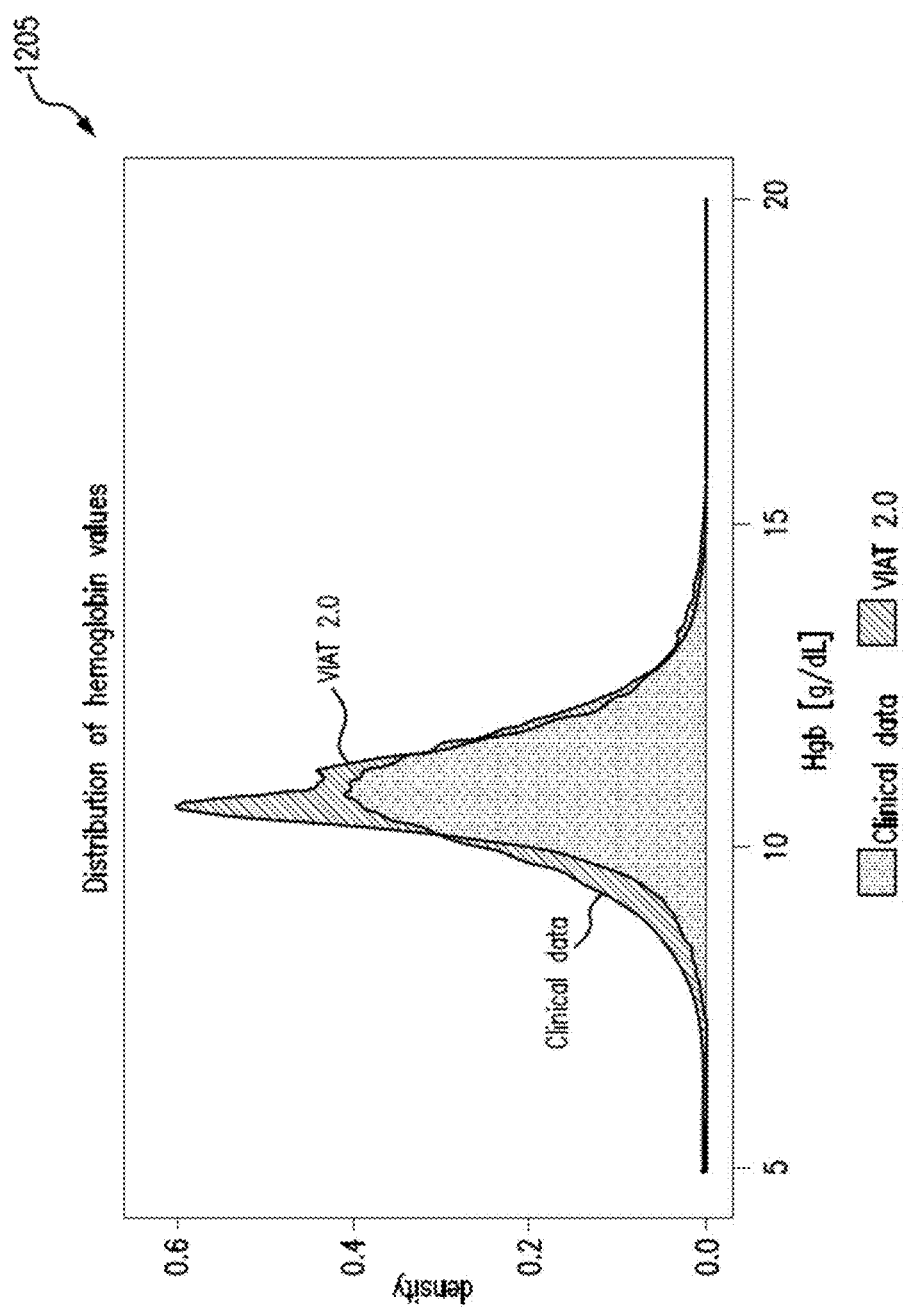
Figure 13:
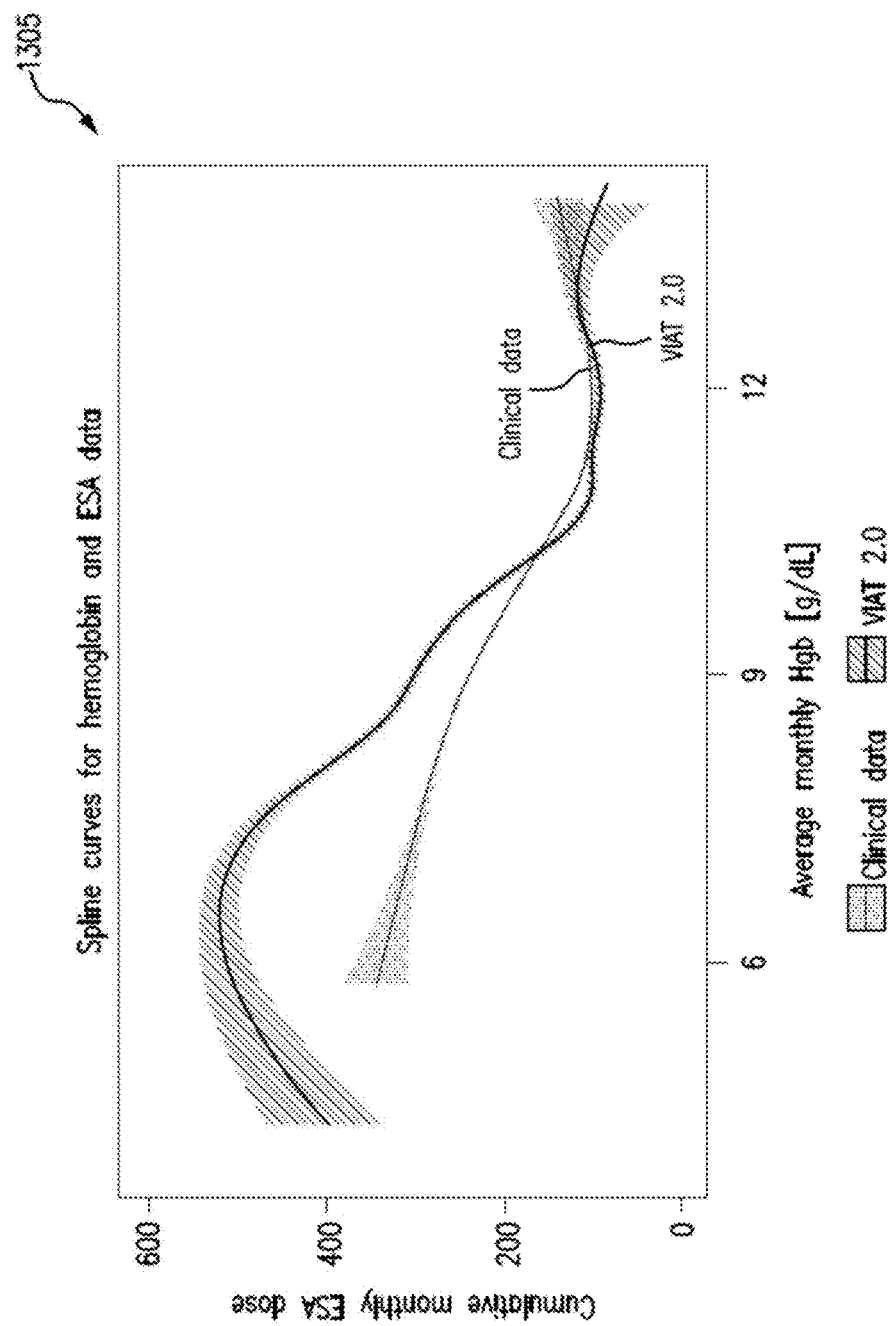

VIAT 2.0 used personalized avatars to improve external validity of the VIAT. For VIAT 2.0, a population of 6,659 avatars was created using routinely collected clinical data from individual HD patients treated for anemia. The avatars were subjected to the same anemia treatment protocol used in the dialysis clinics. Weekly Hgb values were simulated for each avatar and ESA dose adjustments were made following the same protocol used in the VIAT 1.0. Referring to Table 2 of FIG. 18, VIAT 2.0 demonstrated a predicted ESA use per patient-year that underestimated the clinical data by a mere 5.1%. Moreover, ESA dose distributions mirrored empirical characteristics closely (see graph 1105 of FIG. 11). However, the simulated Hgb distribution showed some clear deviations in the 10-11 g/dl range (see graph 1205 of FIG. 12). A closer look at the spline curve for the monthly average hemoglobin values at the monthly cumulative ESA doses (both determined on a per patient level) revealed a relatively wide gap between predicted and real ESA use in the lower Hgb range (<10 g/dl) (see graph 1305 of FIG. 13). The mean ESA dose per HD-treatment was 22.5 mcg in the VIAT 2.0 and 19.5 mcg in the empirical data for patients with an average monthly Hgb of 8-10 g/dl (see Table 2 of FIG. 18). For patients with an average monthly Hgb of <8 g/dl the gap was even more pronounced with a difference in the per HD-treatment ESA dose of 12.1 mcg (39.9 mcg vs 27.8 mcg).

For VIAT 3.0, the Avatar population was subjected to the identical anemia treatment protocol as in Trials 1.0 and 2.0. In VIAT 3.0, clinic modules according to some embodiments were used in the simulations to increase ecological validity (see, for example, FIG. 6). These modules were of stochastic nature and reflected important aspects of clinical routine. For instance, a laboratory module was designed to add noise patterns to simulated Hgb levels to reflect both the measurement noise of the laboratory device and the varying fluid status of the patient. Possible shipment delays of blood samples were included, to simulate the fact that a small fraction of blood samples that arrive at the laboratory are unusable.

Figure 14:
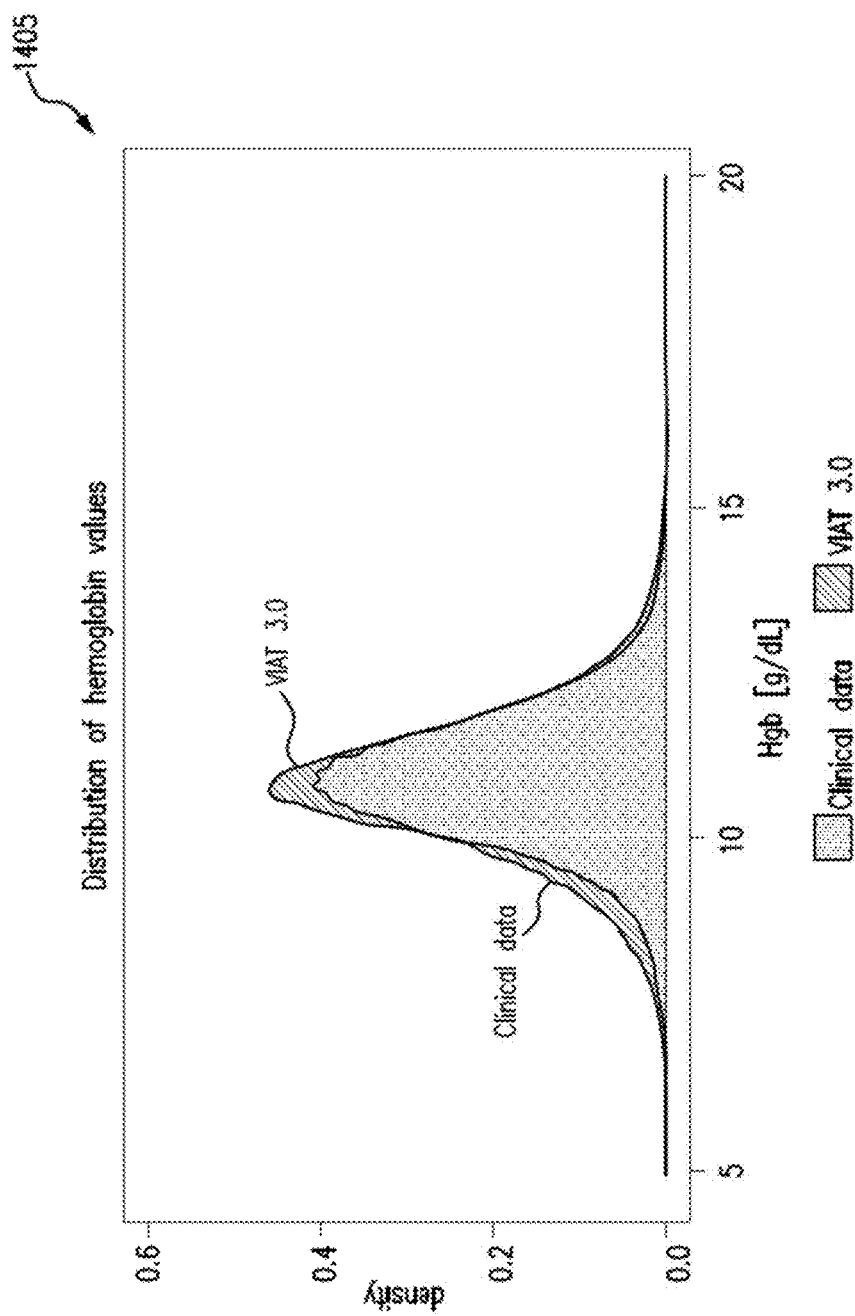
FIGS. 14-16 illustrate graphs of exemplary comparative results of an experimental VIAT 3.0.
Figure 15:
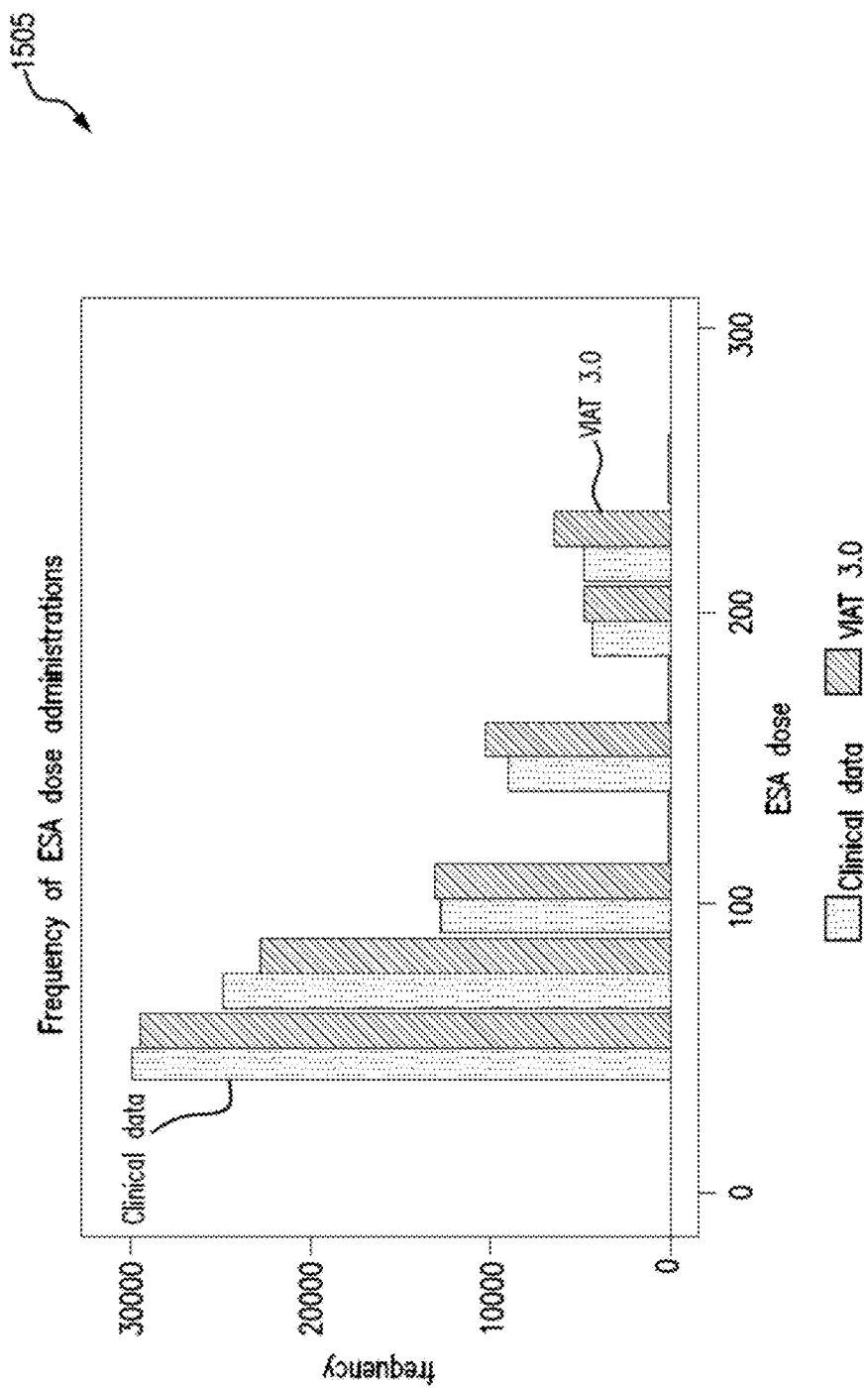
Figure 16:
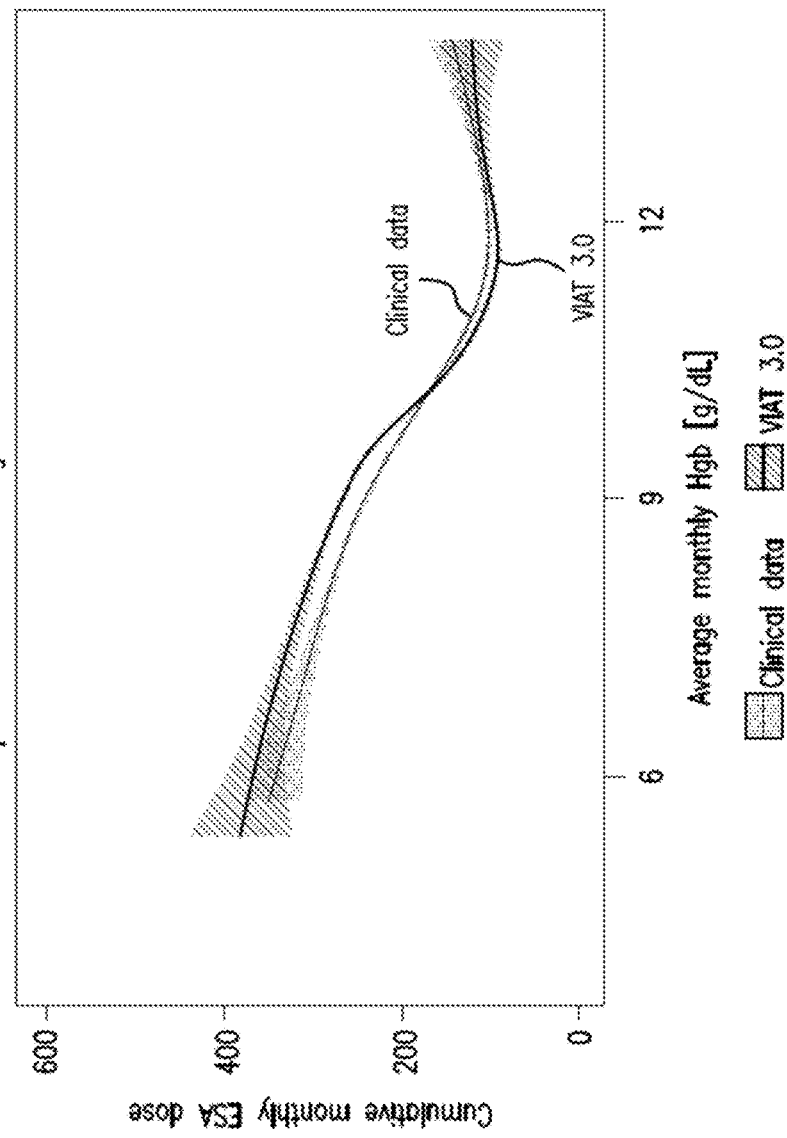

Incorporating several clinically relevant modules improved the predictions of the in silico trial of VIAT 3.0 considerably. For example, the artificial Hgb distributions resembled clinical data exceptionally well (see graph 1405 of FIG. 14). The mean Hgb was slightly higher than in the empirical data, with an overall narrower distribution of observed Hgb values in the in silico data (mean±standard deviation: 10.9±1.1 g/dl vs. 10.8±1.1 g/dl). Further, predicted ESA showed good alignment with clinical data (see graph 1505 of FIG. 15). The median ESA dose per treatment was underestimated by 2.5%, and the cumulative ESA dose per patient-year was underestimated by 5.4% (see Table 2 of FIG. 18). Moreover, spline curves of predicted monthly average hemoglobin vs. monthly cumulative ESA dose further highlighted the excellent agreement between simulated and empirically observed data over the entire Hgb range (see graph 1605 of FIG. 16). Specifically, the difference between predicted vs clinic data in the low Hgb range that was apparent in the VIAT 2.0 was no longer present after including the clinic modules. Average per treatment ESA doses were materially identical in in-silico predictions and clinical data in low Hgb ranges, with 19.4 mcg vs. 19.5 mcg in the 8-10 g/dl Hgb range and 27.3 mcg vs 27.8 mcg in the <8 g/dl Hgb range (see Table 3 of FIG. 19 and Table 4 of FIG. 20).

Accordingly, proactively addressing the questions of external and ecological validity in the design of an in silico trial (for instance, a VAT according to some embodiments) can significantly improve its predictive power. In particular, VAT 3.0 clearly outperformed other designs both with respect to the big picture (for instance, Hgb level distribution, ESA use per patient-year) as well as more granular metrics (for example, number of ESA administrations in different Hgb categories).

Figure 21:
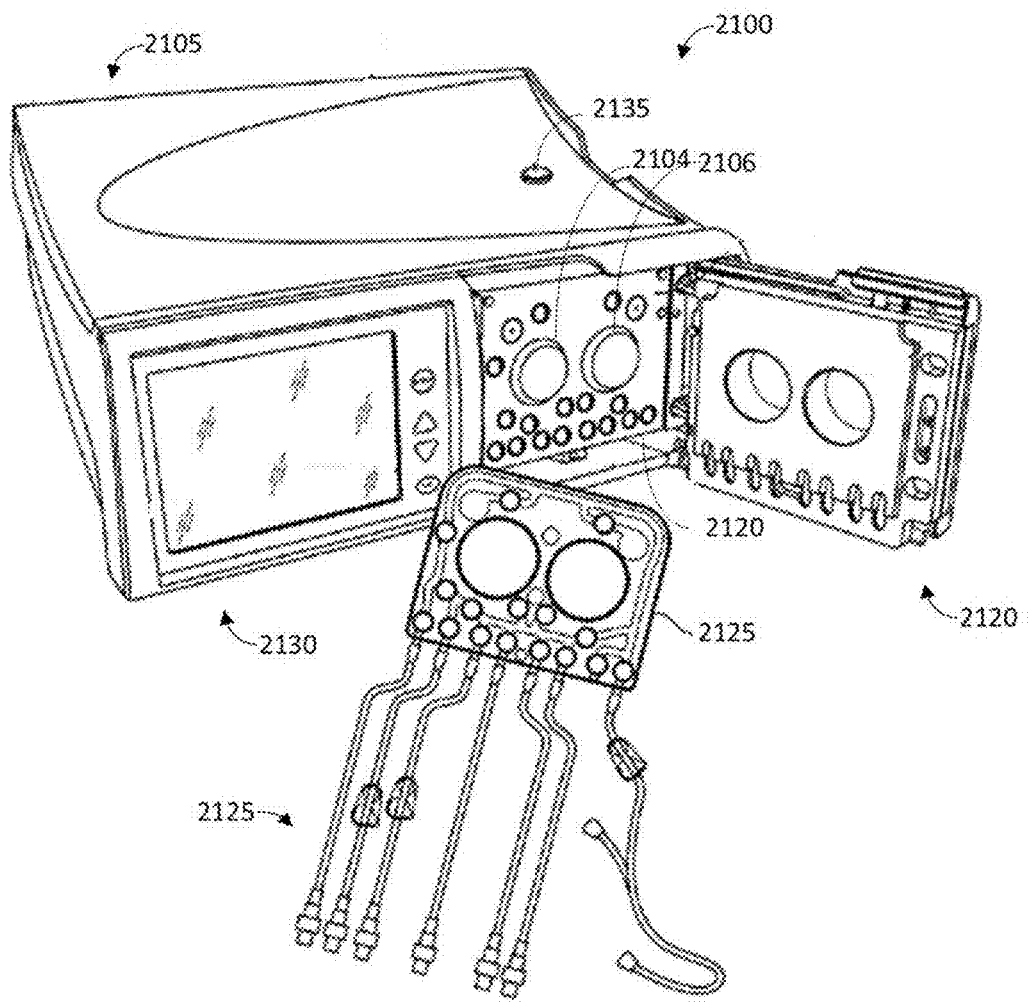
FIG. 21 illustrates an example dialysis device.

Referring now to FIG. 21, a dialysis machine 2100 according to an embodiment of the present disclosure is shown. The machine 2100 may include a housing 2105, a door 2110 for receiving a cartridge 2115 in a cavity 2120, and a user interface portion 2130. Fluid lines 2125 may be coupled to the cartridge in a known manner, such as via a connector, and may further include valves for controlling fluid flow to and from fluid bags including fresh dialysate and warming fluid. In another embodiment, at least a portion of fluid lines 2125 may be integral to cartridge 2115. Prior to operation, a user may open door 2110 to insert a new cartridge 2115 and/or to remove a used cartridge 2115 after operation.

Cartridge 2115 may be placed in cavity 2120 of machine 2100 for operation. During operation, dialysate fluid may be flowed into a patient's abdomen via cartridge 2115, and spent dialysate, waste, and/or excess fluid may be removed from the patient's abdomen via cartridge 2115. Door 2110 may be securely closed to machine 2100. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

User interface portion 2130 may be a touch screen, and may include one or more buttons for selecting and/or entering user information. User interface portion 2130 may be operatively connected to a controller (not shown) and disposed in machine 2100 for receiving and processing the inputs to operate dialysis machine 2100.

In some embodiments, machine 2100 may wirelessly transmit (for example, via a wireless connection), alternatively or simultaneously or in coordination with sending information to computing device 210, healthcare exchange platform 205, and/or integrated care system 305 and/or 405, information or alerts to a remote location, including but not limited to a doctor's office, hospital, call center, and technical support. For example, machine 2100 may provide real time remote monitoring of machine operation and patient parameters determined according to some embodiments. Machine 2100 may include a memory, such as memory 130, to store data and/or machine 2100 may transmit data to a local or remote server at scheduled intervals. For example, machine 2100 may send patient data to computing device 210, healthcare exchange platform 205, and/or integrated care system 305 and/or 405, for use in the one or more algorithms, processes, and/or the like as data associated with a VIAT according to some embodiments.

Figure 22:
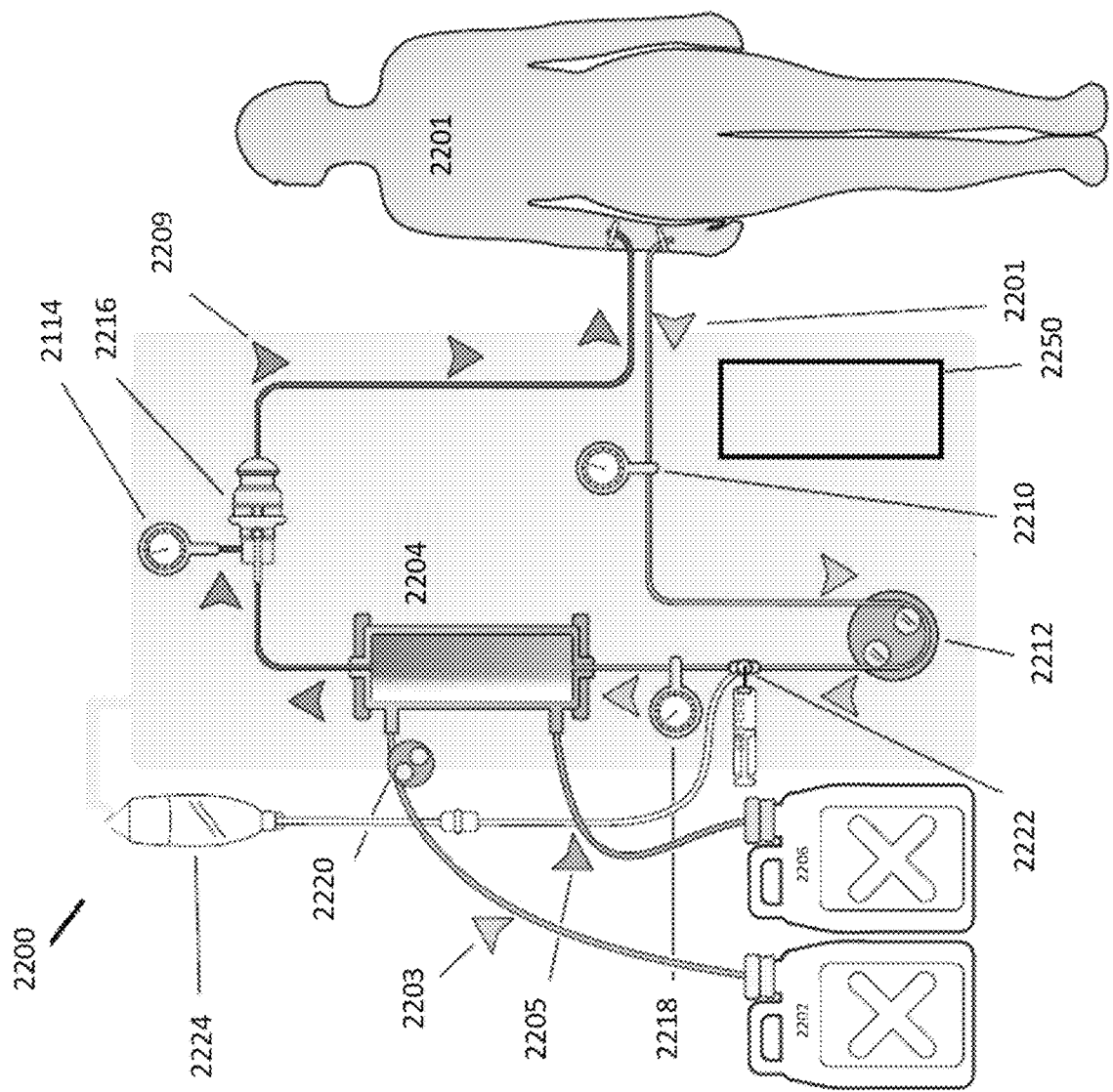
FIG. 22 illustrates an example dialysis system.

FIG. 22 illustrates a diagram of an exemplary embodiment of a dialysis system 2200 in accordance with the present disclosure. Dialysis system 2200 may be configured to provide hemodialysis (HD) treatment for a patient 2201. Fluid reservoir 2202 may deliver fresh dialysate to a dialyzer 2204 via tubing 2203, and reservoir 2206 may receive spent dialysate once it has passed through dialyzer 2204 via tubing 2205. A hemodialysis operation may filter particulates and/or contaminates from a patient's blood through a patient external filtration device, for example, a dialyzer 2204. As the dialysate is passed through dialyzer 2204, unfiltered patient blood is also passed into dialyzer 2204 via tubing 2207 and filtered blood is returned to patient 2201 via tubing 2209. Arterial pressure may be monitored via pressure sensor 2210, inflow pressure monitored via sensor 2218, and venous pressure monitored via pressure sensor 2214. An air trap and detector 2216 may ensure that air is not introduced into patient blood as it is filtered and returned to patient 2201. The flow of blood and the flow of dialysate may be controlled via respective pumps, including a blood pump 2212 and a fluid pump 2220. Heparin 2222, a blood thinner, may be used in conjunction with saline 2224 to ensure blood clots do not form or occlude blood flow through the system.

In some embodiments, dialysis system 2200 may include a controller 2250, which may be similar to computing device 110 and/or components thereof (for instance, processor circuitry 220). Controller 2250 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. In various embodiments, controller may receive and/or calculate information associated with a VIAT. Controller 2250 may also be operatively connected to and/or communicate with additional sensors or sensor systems, devices, and/or the like although controller 2250 may use any of the data available on the patient's biologic functions or other patient parameters. For example, controller 2250 may send patient data to computing device 110, healthcare exchange platform 205, and/or integrated care system 305 and/or 405 to determine VIAT parameters, designs or protocols, compile or analysis results, determine treatments and predict outcomes, and/or the like, according to some embodiments. Machine 2200 and/or components thereof, such as controller 2250, may be operably coupled to various measurement devices, such as a blood pressure device and/or a bioimpedence device, to determine information and/or to provide data to facilitate the determination of information by computing device 110, healthcare exchange platform 205, and/or integrated care system 305 and/or 405.

Figure 23:
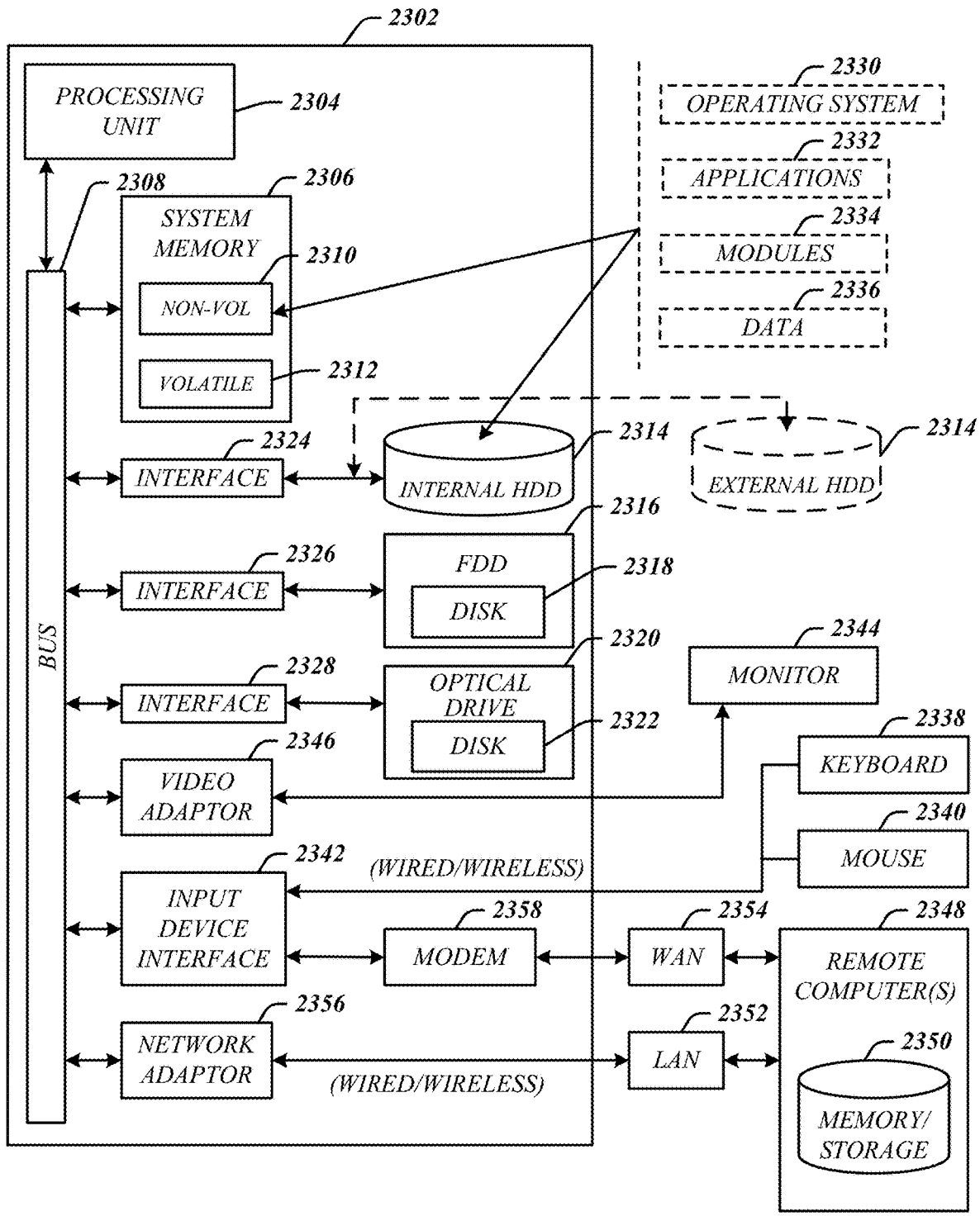
FIG. 23 illustrates an embodiment of a computing architecture.

FIG. 23 illustrates an embodiment of an exemplary computing architecture 2300 suitable for implementing various embodiments as previously described. In various embodiments, the computing architecture 2300 may comprise or be implemented as part of an electronic device. In some embodiments, the computing architecture 2300 may be representative, for example, of computing device 110 and/or components of healthcare exchange platform 205 and/or integrated care system 305 and/or 405. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 2300. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 2300 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 2300.

As shown in FIG. 23, the computing architecture 2300 comprises a processing unit 2304, a system memory 2306 and a system bus 23023. The processing unit 2304 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 2304.

The system bus 23023 provides an interface for system components including, but not limited to, the system memory 2306 to the processing unit 2304. The system bus 23023 can be any of several types of bus structure that may further interconnect to a memory bus (with or without a memory controller), a peripheral bus, and a local bus using any of a variety of commercially available bus architectures. Interface adapters may connect to the system bus 23023 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 2306 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 23, the system memory 2306 can include non-volatile memory 2310 and/or volatile memory 2312. A basic input/output system (BIOS) can be stored in the non-volatile memory 2310.

The computer 2302 may include various types of computer-readable storage media in the form of one or more lower speed memory units, including an internal (or external) hard disk drive (HDD) 2314, a magnetic floppy disk drive (FDD) 2316 to read from or write to a removable magnetic disk 23123, and an optical disk drive 2320 to read from or write to a removable optical disk 2322 (e.g., a CD-ROM or DVD). The HDD 2314, FDD 2316 and optical disk drive 2320 can be connected to the system bus 23023 by a HDD interface 2324, an FDD interface 2326 and an optical drive interface 23223, respectively. The HDD interface 2324 for external drive implementations can include at least one or both of Universal Serial Bus (USB) and IEEE 23234 interface technologies.

The drives and associated computer-readable media provide volatile and/or nonvolatile storage of data, data structures, computer-executable instructions, and so forth. For example, a number of program modules can be stored in the drives and memory units 2310, 2312, including an operating system 2330, one or more application programs 2332, other program modules 2334, and program data 2336. In one embodiment, the one or more application programs 2332, other program modules 2334, and program data 2336 can include, for example, the various applications and/or components of apparatus 105, 205, 305, and/or 405.

A user can enter commands and information into the computer 2302 through one or more wire/wireless input devices, for example, a keyboard 23323 and a pointing device, such as a mouse 2340. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 2304 through an input device interface 2342 that is coupled to the system bus 23023, but can be connected by other interfaces such as a parallel port, IEEE 2394 serial port, a game port, a USB port, an IR interface, and so forth.

A monitor 2344 or other type of display device is also connected to the system bus 23023 via an interface, such as a video adaptor 2346. The monitor 2344 may be internal or external to the computer 802. In addition to the monitor 2344, a computer typically includes other peripheral output devices, such as speakers, printers, and so forth.

The computer 2302 may operate in a networked environment using logical connections via wire and/or wireless communications to one or more remote computers, such as a remote computer 23423. The remote computer 23423 can be a workstation, a server computer, a router, a personal computer, portable computer, microprocessor-based entertainment appliance, a peer device or other common network node, and typically includes many or all of the elements described relative to the computer 2302, although, for purposes of brevity, only a memory/storage device 2350 is illustrated. The logical connections depicted include wire/wireless connectivity to a local area network (LAN) 2352 and/or larger networks, for example, a wide area network (WAN) 2354. Such LAN and WAN networking environments are commonplace in offices and companies, and facilitate enterprise-wide computer networks, such as intranets, all of which may connect to a global communications network, for example, the Internet.

When used in a LAN networking environment, the computer 2302 is connected to the LAN 2352 through a wire and/or wireless communication network interface or adaptor 2356. The adaptor 2356 can facilitate wire and/or wireless communications to the LAN 2352, which may also include a wireless access point disposed thereon for communicating with the wireless functionality of the adaptor 2356.

When used in a WAN networking environment, the computer 2302 can include a modem 23523, or is connected to a communications server on the WAN 2354, or has other means for establishing communications over the WAN 2354, such as by way of the Internet. The modem 23523, which can be internal or external and a wire and/or wireless device, connects to the system bus 23023 via the input device interface 2342. In a networked environment, program modules depicted relative to the computer 2302, or portions thereof, can be stored in the remote memory/storage device 2350. It will be appreciated that the network connections shown are exemplary and other means of establishing a communications link between the computers can be used.

The computer 2302 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
   at least one memory storing instructions; and
   at least one processor coupled to the at least one memory, the at least one processor, responsive to executing the instructions, to cause the apparatus to:
   access a plurality of patient avatars configured to model an anemia health condition of a patient,
   access a virtual clinical trial configured to simulate at least one course of treatment for the plurality of patient avatars, the virtual clinical trial comprising a virtual anemia trial, and
   execute the virtual anemia trial for the plurality of patient avatars to simulate a treatment protocol for anemia to generate simulation results via, for each of the plurality of avatars during a course of treatment:
   advancing virtual information of an avatar through a series of clinic modules, each of the series of clinic modules configured to model an operational aspect of an entity associated with the virtual anemia trial, the series of clinic modules comprising software modules,
   performing an occurrence of an event associated with the entity based on a probability for the event configured in one of the series of clinic modules, and
   generating at least one event result representing a consequence of the occurrence of the event, wherein the simulation results are calculated based, at least in part, on the at least one event result.

2. The apparatus of claim 1, each of the plurality of avatars comprising a physiology-based mathematical model configured to simulate treatment results following a round of virtual treatment via emulating a development of red blood cells for a particular dialysis patient and an effect of a dosage of an erythropoiesis stimulating agent (ESA) on the development of the red blood cells.

3. The apparatus of claim 1, the series of clinical modules comprising at least one stochastic module.

4. The apparatus of claim 1, the series of clinical modules comprising at least one of a hospital module, a physician module, a laboratory module, or a dialysis facility module.

5. The apparatus of claim 1, the series of clinical modules comprising a laboratory module, and the at least one event comprising at least one of measurement noise or unusable samples.

6. The apparatus of claim 1, the series of clinical modules comprising a physician module, and the at least one event comprising a physician decision.

7. The apparatus of claim 1, the at least one event comprising hospitalization.

8. The apparatus of claim 1, the virtual information comprising a virtual blood sample of the avatar.

9. The apparatus of claim 1, the at least one processor, responsive to executing the instructions, to cause the apparatus to determine the probability of the at least event based on real-world clinical data.

10. The apparatus of claim 1, the at least one processor, responsive to executing the instructions, to cause the apparatus to determine a course of a real-world clinical trial based on the simulation results.

11. The apparatus of claim 1, the at least one processor, responsive to executing the instructions, to cause the apparatus to generate a recommended course of treatment based on the simulation results.

12. The apparatus of claim 1, the at least one processor, responsive to executing the instructions, to cause the apparatus to:
receive user input creating a new event for one of the series of clinic modules, the user input defining an event result and a probability for the new event, and
modify the one of the series clinic modules to perform the new event based on the probability.

13. The apparatus of claim 1, the at least one processor, responsive to executing the instructions, to cause the apparatus to:
analyze the simulation results for at least one of the plurality of patient avatars responsive to completion of a specified time period of the course of treatment; and
modify at least one treatment parameter based on the simulation results for the specified time period.

14. The apparatus of claim 2, the virtual anemia trial to simulate a treatment protocol comprising providing ESA for anemia.

15. A method, comprising, via at least one processor of a computing device:
accessing a plurality of patient avatars configured to model an anemia health condition of a patient;
accessing a virtual clinical trial configured to simulate at least one course of treatment for the plurality of patient avatars, the virtual clinical trial comprising a virtual anemia trial; and
executing the virtual anemia trial for the plurality of patient avatars to simulate a treatment protocol for anemia to generate simulation results via, for each of the plurality of avatars during a course of treatment:
advancing virtual information of an avatar through a series of clinic modules, each of the series of clinic modules configured to model an operational aspect of an entity associated with the virtual anemia trial, the series of clinic modules comprising software modules,
performing an occurrence of an event associated with the entity based on a probability for the event configured in one of the series of clinic modules, and
generating at least one event result representing a consequence of the occurrence of the event, wherein the simulation results are calculated based, at least in part, on the at least one event result.

16. The method of claim 15, the plurality of avatars comprising a physiology-based mathematical model configured to simulate treatment results following a round of virtual treatment via emulating a development of red blood cells for a particular dialysis patient and an effect of a dosage of an erythropoiesis stimulating agent (ESA) on the development of the red blood cells.

17. The method of claim 15, the series of clinical modules comprising at least one of a hospital module, a physician module, a laboratory module, or a dialysis facility module.

18. The method of claim 15, the at least one event comprising at least one of measurement noise, unusable samples, a physician decision, or hospitalization.

19. The method of claim 15, the at least one processor, responsive to executing the instructions, to cause the apparatus to
determine a course of a real-world clinical trial based on the simulation results.

20. The method of claim 16, the virtual anemia trial to simulate a treatment protocol comprising providing ESA for anemia.

* * * * *